United States Patent
Oh et al.

(10) Patent No.: US 9,538,984 B2
(45) Date of Patent: Jan. 10, 2017

(54) COMBINED IMAGING APPARATUS AND METHOD FOR CONTROLLING THE SAME

(71) Applicant: SAMSUNG MEDISON CO., LTD., Hongcheon-gun, Gangwon-do (KR)

(72) Inventors: Jung Taek Oh, Seoul (KR); Jong Kyu Jung, Seoul (KR)

(73) Assignee: SAMSUNG MEDISON CO., LTD., Hongcheon-gun, Gangwon-do (KR)

( * ) Notice: Subject to any disclaimer, the term of this patent is extended or adjusted under 35 U.S.C. 154(b) by 342 days.

(21) Appl. No.: 14/176,962

(22) Filed: Feb. 10, 2014

(65) Prior Publication Data
US 2014/0236007 A1 Aug. 21, 2014

(30) Foreign Application Priority Data
Feb. 19, 2013 (KR) .................... 10-2013-0017703

(51) Int. Cl.
*A61B 8/00* (2006.01)
*A61B 5/00* (2006.01)

(52) U.S. Cl.
CPC ........... *A61B 8/4416* (2013.01); *A61B 5/0035* (2013.01); *A61B 5/0095* (2013.01); *A61B 2560/0266* (2013.01)

(58) Field of Classification Search
CPC .... A61B 8/4416; A61B 5/0035; A61B 5/0095
See application file for complete search history.

(56) References Cited

U.S. PATENT DOCUMENTS

| | | | |
|---|---|---|---|
| 2006/0084871 A1* | 4/2006 | Akaki | A61B 8/13 600/437 |
| 2009/0054763 A1 | 2/2009 | Wang et al. | |
| 2009/0105588 A1* | 4/2009 | Emelianov | A61B 5/4869 600/438 |
| 2014/0275941 A1* | 9/2014 | Kang | A61B 5/7278 600/407 |

FOREIGN PATENT DOCUMENTS

| | | |
|---|---|---|
| JP | 2012-152267 A | 8/2012 |
| KR | 10-2006-0080562 A | 7/2006 |

OTHER PUBLICATIONS

Korean Office Action dated Apr. 3, 2014, issued in corresponding Korean Patent Application No. 10-2013-0017703. 6 pgs.

\* cited by examiner

*Primary Examiner* — Peter Luong
(74) *Attorney, Agent, or Firm* — McDermott Will & Emery LLP

(57) ABSTRACT

A combined imaging apparatus in which heterogeneous imaging devices are combined and a method for controlling the same are disclosed. The combined imaging apparatus includes a photoacoustic imaging unit to irradiate an energy beam to a target part, an ultrasonic imaging unit to generate an ultrasonic wave, irradiate the ultrasonic wave to the target part, and collect an echo ultrasonic wave reflected from the target part to which the ultrasonic wave is irradiated or an ultrasonic wave generated from the target part in response to energy beam irradiation of the photoacoustic imaging unit. The ultrasonic imaging unit starts or stops operation according to an operation state of the photoacoustic imaging unit.

26 Claims, 19 Drawing Sheets

FIG. 8A

|   | STATE OF PHOTOACOUSTIC IMAGING UNIT | STATE OF ULTRASONIC IMAGING UNIT |
|---|---|---|
| 1 | STOP STATE | OPERATION OF ULTRASONIC IMAGING UNIT |
| 2 | ACTIVE STATE | STOP OPERATION OF ULTRASONIC IMAGING UNIT |
| 3 | PRE-ACTIVE STATE | STOP OPERATION OF STATE ULTRASONIC IMAGING UNIT |
| 4 | | READY TO OPERATE ULTRASONIC IMAGING UNIT |

FIG. 8B

| | STATE OF PHOTOACOUSTIC IMAGING UNIT | STATE OF ULTRASONIC IMAGING UNIT | |
|---|---|---|---|
| 1 | STOP STATE | OPERATION OF ULTRASONIC IMAGING UNIT | |
| 2 | ACTIVE STATE | CASE IN WHICH ULTRASONIC IMAGING UNIT DOES NOT COLLECT ECHO ULTRASONIC WAVES, OR CASE AFTER COLLECTION OF ECHO ULTRASONIC WAVES | CASE IN WHICH OPERATION OF ULTRASONIC IMAGING UNIT IS MAINTAINED, ECHO ULTRASONIC WAVES ARE COLLECTED AND THE ULTRASONIC IMAGING UNIT STOPS OPERATION |
| 3 | | CASE BEFORE ULTRASONIC IMAGING UNIT COLLECTS ECHO ULTRASONIC WAVES | STOP OPERATION OF ULTRASONIC IMAGING UNIT |
| 4 | PRE-ACTIVE STATE | CASE IN WHICH ULTRASONIC IMAGING UNIT DOES NOT COLLECT ECHO ULTRASONIC WAVES, OR CASE AFTER COLLECTION OF ECHO ULTRASONIC WAVES | CASE IN WHICH OPERATION OF ULTRASONIC IMAGING UNIT IS MAINTAINED, ECHO ULTRASONIC WAVES ARE COLLECTED AND THE ULTRASONIC IMAGING UNIT STOPS OPERATION |
| 5 | | CASE BEFORE ULTRASONIC IMAGING UNIT COLLECTS ECHO ULTRASONIC WAVES | STOP OPERATION OF ULTRASONIC IMAGING UNIT |
| 6 | | | |

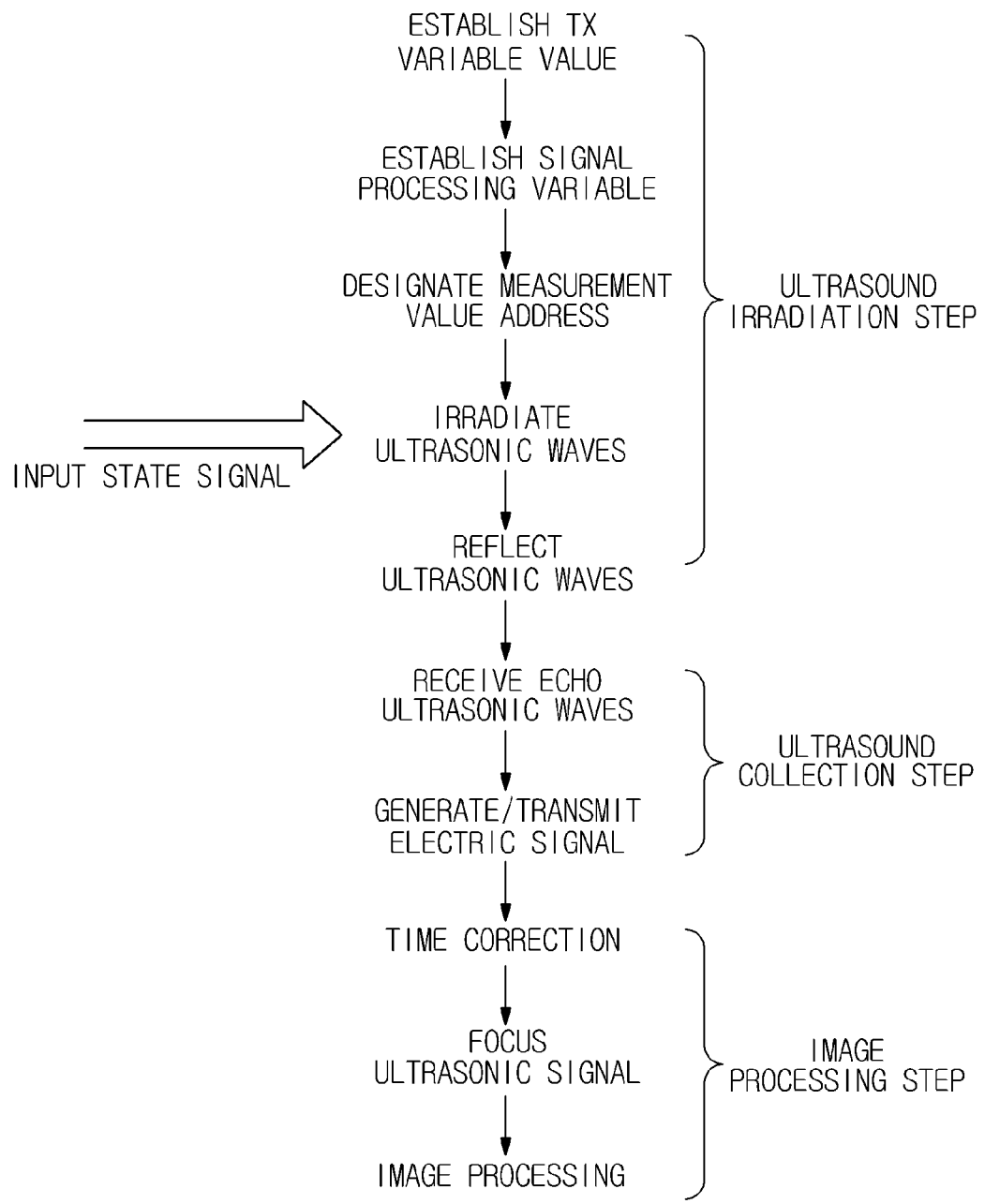

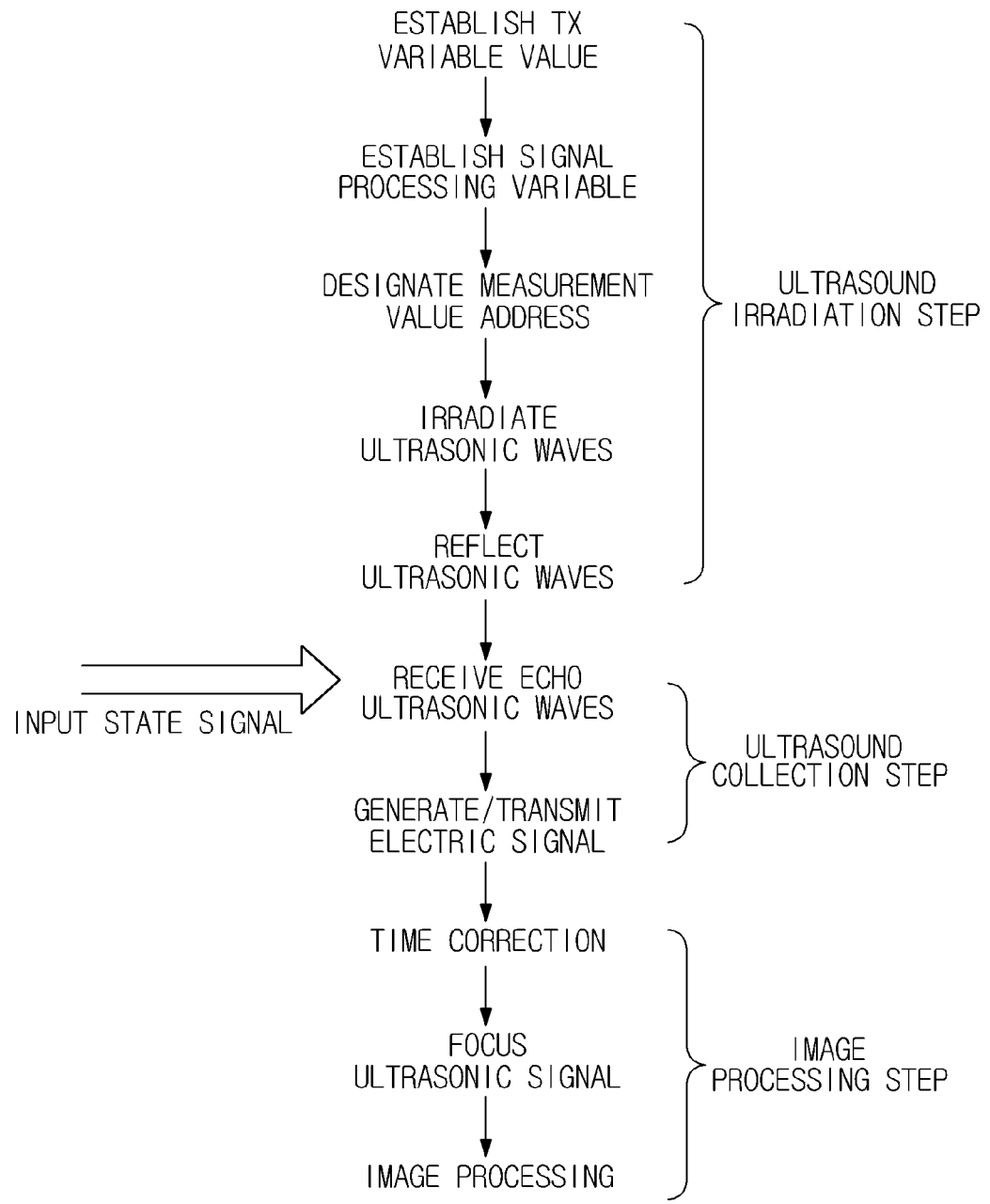

COMBINED IMAGING APPARATUS AND METHOD FOR CONTROLLING THE SAME

CROSS-REFERENCE TO RELATED APPLICATION

This application claims priority from Korean Patent Application No. 2013-0017703, filed on Feb. 19, 2013 in the Korean Intellectual Property Office, the disclosure of which is incorporated herein by reference in its entirety.

BACKGROUND

1. Field

One or more exemplary embodiments relate to a combined imaging apparatus in which heterogeneous imaging apparatuses are combined, and a method for controlling the same.

2. Description of the Related Art

An ultrasonic imaging apparatus receives ultrasonic waves from a target object contacting an ultrasonic probe, focuses the received ultrasonic signal by beam forming the received ultrasonic signal, and performs predetermined image processing on the basis of the focused signal, such that an ultrasonic image is created.

An ultrasonic transducer capable of generating ultrasonic waves is installed at a front end of the ultrasonic probe of the ultrasonic imaging apparatus. The transducer converts one form of energy (for example, electric energy) into another form of energy (for example, vibration or light). The ultrasonic transducer located at the front end of the ultrasonic probe vibrates in response to a general input pulse current so as to generate ultrasonic waves. In addition, the ultrasonic transducer vibrates in response to received external ultrasonic waves so that a predetermined electric signal having a specific pulse is generated.

The ultrasonic imaging apparatus focuses the generated electric signal, generates an ultrasonic image on the basis of the focused signal, obtains an ultrasonic image showing an internal image of the target object, and displays the obtained ultrasonic image to a user such as a doctor or patient.

If a laser beam is focused on a target part of a target object, acoustic waves such as ultrasonic waves are generated from the target part. In this case, the ultrasonic transducer of the ultrasonic probe receives the acoustic waves generated by laser, such that it may generate an ultrasonic image showing an internal image of the target object using the same or similar process as described above.

SUMMARY

Therefore, it is an aspect of one or more exemplary embodiments to provide a combined imaging apparatus and a method for controlling the same.

It is another aspect of one or more exemplary embodiments to provide a combined imaging apparatus in which a photoacoustic imaging apparatus configured to generate ultrasonic waves from a target part by emitting an energy beam to the target part is combined with an ultrasonic imaging apparatus for emitting ultrasonic waves to the target part and receiving echo ultrasonic waves reflected from the target part. The combined imaging apparatus removes image distortion, caused by overlap or collision of at least two operations of individual heterogeneous imaging apparatuses, from a measured image, resulting in improved image accuracy.

It is another aspect of one or more exemplary embodiments to provide a combined imaging apparatus to prevent a standby time needed for image capture of at least one heterogeneous imaging apparatus from being unnecessarily delayed due to a variance in measurement time generated when the heterogeneous imaging apparatuses are simultaneously operated.

It is another aspect of one or more exemplary embodiments to provide a combined imaging apparatus for preventing overlap or collision between operations of the heterogeneous imaging apparatuses, and solving inconvenience of a user who has to make a complicated time schedule and associated algorithms needed for simultaneously controlling a heterogeneous imaging apparatuses to prevent the occurrence of distortion of a measured image.

It is another aspect of one or more exemplary embodiments to provide a combined imaging apparatus capable of time-based independent control of individual heterogeneous imaging apparatuses.

Accordingly, embodiments are directed to a combined imaging apparatus and a method for controlling the same that substantially obviate one or more problems due to limitations and disadvantages of the related art.

Additional aspects of one or more exemplary embodiments will be set forth in part in the description which follows and, in part, will be obvious from the description, or may be learned by practice of the invention.

In accordance with one aspect of one or more exemplary embodiments, a combined imaging apparatus includes: a photoacoustic imaging unit to irradiate an energy beam to a target part; an ultrasonic imaging unit to generate an ultrasonic wave, irradiate the ultrasonic wave to the target part, and collect an echo ultrasonic wave reflected from the target part to which the ultrasonic wave is irradiated or an ultrasonic wave generated from the target part in response to energy beam irradiation of the photoacoustic imaging unit, wherein the operation of the ultrasonic imaging unit is decided according to an operation state of the photoacoustic imaging unit.

The photoacoustic imaging unit and the ultrasonic imaging unit may be controlled on the basis of a state-signal based control sequence. The ultrasonic imaging unit may start or stop operation on the basis of an operation state of the photoacoustic imaging unit while the photoacoustic imaging unit and the ultrasonic imaging unit are operated according to the state-signal based control sequence.

The photoacoustic imaging unit may be in an active state for energy beam irradiation or in a pre-active state indicating a ready state for energy beam irradiation.

If the photoacoustic imaging unit may be in the active state or in the pre-active state, the ultrasonic imaging unit may stop an ultrasound irradiation, etc.

The operation of the ultrasonic imaging unit is decided in response to a current operation state of the ultrasonic imaging unit. If the ultrasonic imaging unit collects the echo ultrasonic waves under the condition that the photoacoustic imaging unit is in the pre-active state, the operation for collecting the echo ultrasonic waves by the ultrasonic imaging unit may be maintained. If the operation for collecting echo ultrasonic waves by the ultrasonic imaging unit is ended, the ultrasonic imaging unit may stop operation.

If the photoacoustic imaging unit is in the active state for energy beam irradiation, the ultrasound imaging unit does not perform ultrasound irradiation, and collects ultrasonic signals generated from a target part in response to an energy beam, such that an ultrasonic image can be generated and output.

If the photoacoustic imaging unit is in the active state or in the pre-active state, the photoacoustic imaging unit may output a state signal indicating the operation state of the photoacoustic imaging unit. If the photoacoustic imaging unit does not output the state signal, the ultrasonic imaging unit may perform the ultrasound irradiation operation. If the photoacoustic imaging unit outputs a state signal indicating the active state, ultrasound irradiation may stop operation ad ultrasound collection may stop operation. If the photoacoustic imaging unit outputs a state signal indicating the pre-active state, the ultrasound irradiation operation and the ultrasound collection operation are continuously performed. Thereafter, if the ultrasound collection operation is completed, the ultrasound irradiation stops operation.

If the photoacoustic imaging unit is in an active state for energy beam irradiation or in a pre-active state, the number of operation times of the ultrasonic imaging unit may be decided. The ultrasonic imaging unit may operate according to the decided number of operation times of the ultrasonic imaging unit.

The photoacoustic imaging unit may include a sensor unit to detect the operation state of the photoacoustic imaging unit. The sensor unit may be a photo sensor for detecting the energy beam irradiated to the target part by the photoacoustic imaging unit.

The photoacoustic imaging unit may generate a state signal indicating the operation state of the photoacoustic imaging unit on the basis of an elapse time.

The ultrasonic imaging unit may collect acoustic waves generated by the target part to which an energy beam from the photoacoustic imaging unit is irradiated.

In accordance with another aspect of one or more exemplary embodiments, a combined imaging apparatus includes: a photoacoustic imaging unit to irradiate an energy beam to a target part; an ultrasonic imaging unit to collect ultrasonic waves generated from the target part to which the energy beam is irradiated, or generate ultrasonic waves and irradiate the ultrasonic waves to the target part, and collect echo ultrasonic waves reflected from the target part to which the ultrasonic waves are irradiated; and a controller to receive a state signal indicating an operation state of the photoacoustic imaging unit, and determine an operation of the ultrasonic imaging unit according to the state signal of the photoacoustic imaging unit.

In accordance with another aspect of one or more exemplary embodiments, a method for controlling a combined imaging apparatus which includes a photoacoustic imaging unit for irradiating an energy beam to a target part, an ultrasonic imaging unit for generating an ultrasonic wave, irradiating the ultrasonic wave to the target part, and collecting an echo ultrasonic wave reflected from the target part to which the ultrasonic wave is irradiated, includes: operating the ultrasonic imaging unit; outputting, by the photoacoustic imaging unit, a state signal indicating an operation state of the photoacoustic imaging unit; and deciding an operation of the ultrasonic imaging unit according to the state signal generated from the photoacoustic imaging unit.

The photoacoustic imaging unit may be in an active state indicating energy beam irradiation or in a pre-active state indicating a ready state for energy beam irradiation.

The deciding the operation of the ultrasonic imaging unit according to the state signal generated from the photoacoustic imaging unit may include: stopping the ultrasound irradiation operation of the ultrasonic imaging unit when the photoacoustic imaging unit is in the active state or in the pre-active state.

The deciding the operation of the ultrasonic imaging unit according to the state signal generated from the photoacoustic imaging unit may include: if the photoacoustic imaging unit is in the active state or in the pre-active state, confirming an operation state of the ultrasonic imaging unit; and deciding an operation of the ultrasonic imaging unit according to the confirmed operation state of the ultrasonic imaging unit.

The deciding the operation of the ultrasonic imaging unit according to the confirmed operation state of the ultrasonic imaging unit may include: if the ultrasonic imaging unit collects echo ultrasonic waves, deciding to continuously operate the ultrasonic imaging unit. The deciding the operation of the ultrasonic imaging unit according to the confirmed operation state of the ultrasonic imaging unit may include: if collection of the echo ultrasonic waves caused by the ultrasonic imaging unit is completed, stopping operation of the ultrasonic imaging unit.

The deciding the operation of the ultrasonic imaging unit according to the state signal generated from the photoacoustic imaging unit may include: if the photoacoustic imaging unit is in an active state or in a pre-active state, deciding the number of operation times of the ultrasonic imaging unit; and operating the ultrasonic imaging unit the decided number of operation times.

The outputting the state signal indicating the operation state of the photoacoustic imaging unit may include: detecting the operation state of the photoacoustic imaging unit by a sensor unit of the photoacoustic imaging unit; and outputting a state signal indicating the operation state of the photoacoustic imaging unit according to the detected result. The sensor unit may be a photo sensor for detecting the energy beam irradiated to the target part by the photoacoustic imaging unit.

The outputting the state signal indicating the operation state of the photoacoustic imaging unit may includes: generating the state signal indicating the photoacoustic imaging unit's operation state generated on the basis of an elapsed time generated after energy beam irradiation (i.e., active state) starts operation.

The method may further include: if the photoacoustic imaging unit does not output the state signal, deciding to operate the ultrasonic imaging unit.

BRIEF DESCRIPTION OF THE DRAWINGS

These and/or other aspects of one or more exemplary embodiments will become apparent and more readily appreciated from the following description of the embodiments, taken in conjunction with the accompanying drawings of which:

FIGS. 8A and 8B are tables illustrating operations of the ultrasonic imaging unit according to an operation state of the photoacoustic imaging unit;

FIGS. 9A and 9B are flowcharts illustrating the case in which a state signal is input during operation of the ultrasonic imaging unit;

DETAILED DESCRIPTION

Figure 1:
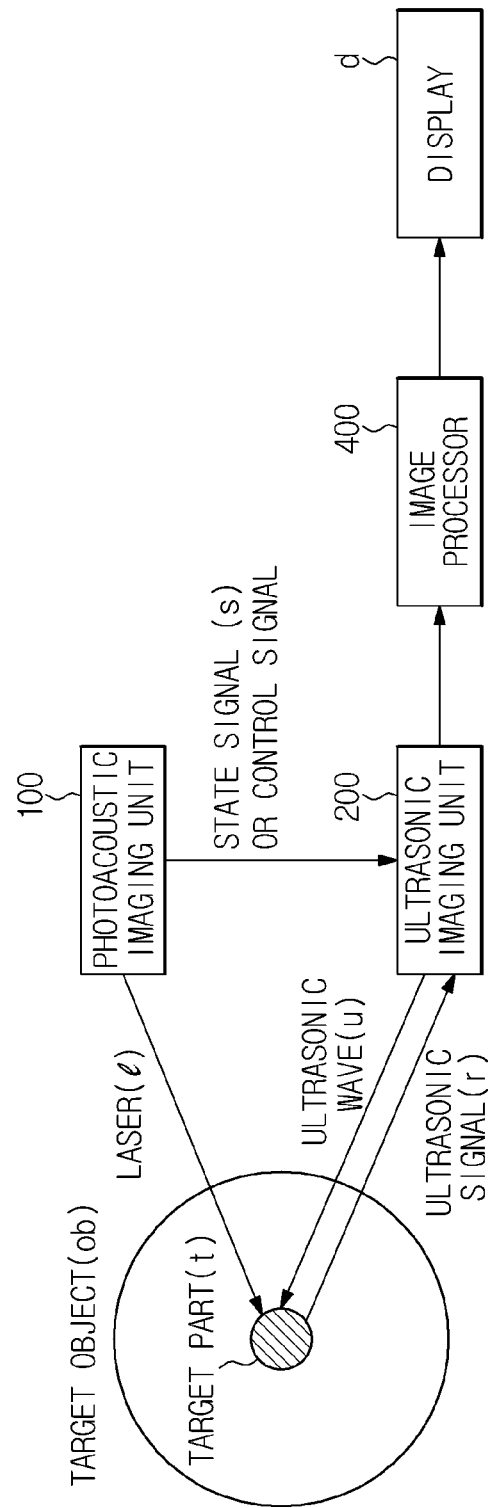
FIG. 1 is a block diagram illustrating a combined imaging apparatus according to one embodiment.

Reference will now be made in detail to the embodiments of one or more exemplary embodiments, examples of which are illustrated in the accompanying drawings, wherein like reference numerals refer to like elements throughout.

FIG. 1 is a block diagram illustrating a combined imaging apparatus according to one embodiment.

Referring to FIG. 1, the combined imaging apparatus may include two different kinds of image-data collectors, for example, a photoacoustic imaging unit 100 and an ultrasonic imaging unit 200.

The photoacoustic imaging unit 100 may irradiate an energy beam (e.g., a pulse laser l) to a target part (t) of a target object (ob) such as a human being. Therefore, the target part (t) of the target object (ob) is heated and expanded by radiation of the laser (l), resulting in the occurrence of an acoustic wave (r) such as an ultrasonic wave. In this way, the ultrasonic wave (r) induced by the laser is collected by an ultrasonic receiver such as an ultrasonic transducer, such that an ultrasonic image is generated on the basis of the collected ultrasonic waves (r).

The ultrasonic imaging unit 200 irradiates ultrasonic waves to the target part (t) of the target object (ob). The ultrasonic waves irradiated by characteristics of the target part (t) are reflected. The ultrasonic imaging unit 200 may receive ultrasonic waves (i.e., echo ultrasonic waves "r") reflected from the target part (t).

The ultrasonic imaging unit 200 may include an ultrasonic probe, may emit ultrasonic waves to the end of a direction of the target object of the ultrasonic probe, or may include an ultrasonic transducer configured to collect ultrasonic waves.

The image processor 400 connected to the ultrasonic imaging unit 200 generates an ultrasonic image through beamforming on the basis of the collected ultrasonic signal (r), and outputs the ultrasonic image through a display (d).

In accordance with one embodiment, in response to the laser (l) irradiated from the photoacoustic imaging unit 100, the photoacoustic imaging unit 100 may allow the same ultrasonic transducer to receive an ultrasonic wave (r) generated from the target part (t) and an echo ultrasonic wave (r) generated when an ultrasonic wave (u) irradiated from the ultrasonic imaging unit 200 is reflected from the target part. In accordance with another embodiment, different ultrasonic transducers may receive individual ultrasonic waves independently of each other.

Assuming that one ultrasonic transducer receives an ultrasonic wave generated by laser and an echo ultrasonic wave reflected from the target part (t), it may be possible for the ultrasonic transducer located at the end of the above ultrasonic imaging unit 200 to simultaneously receive the ultrasonic wave and the echo ultrasonic wave as shown in FIG. 1.

Hereinafter, the embodiment in which the ultrasonic transducer of the ultrasonic imaging unit 200 collects an ultrasonic wave generated by laser and an echo ultrasonic wave reflected from the target part (t) will be given below.

That is, the ultrasonic imaging unit 200 may collect not only an ultrasonic wave generated by laser (l) irradiated from the photoacoustic imaging unit 100, but also an ultrasonic wave (r) generated by reflection of an ultrasonic wave (u) irradiated from the ultrasonic imaging unit 200. In this case, the image processor 400 connected to the ultrasonic imaging unit 200 may generate each ultrasonic image on the basis of each ultrasonic signal (r), such that it displays the ultrasonic image to a user.

Referring to FIG. 1, the photoacoustic imaging unit 100 generates either a state signal (s) indicating a current state of the photoacoustic imaging unit 100 or a control signal based on the state of the photoacoustic imaging unit 100, and then transmits the generated state signal (s) or the control signal to the ultrasonic imaging unit 200.

In this case, the state of the photoacoustic imaging unit 100 based on the state signal (s) or the control signal of the photoacoustic unit 100 may correspond to any one of an active state, a pre-active state, and a stop state.

In this case, the active state may indicate a state in which the photoacoustic imaging unit 100 operates and the target part (t) of the target object (ob) is irradiated with an energy beam such as a laser. The pre-active state may indicate a state in which the photoacoustic imaging unit 100 is ready to emit the energy beam such as the laser. That is, the pre-active state may indicate a specific state provided before the photoacoustic imaging unit 100 irradiates the laser to the target part or another state provided before reaching a predetermined time for laser irradiation. The stop state may indicate that the photoacoustic imaging unit 100 does not operate or may indicate a state provided after the target part is irradiated with the laser or another state provided when the photoacoustic imaging unit 100 does not irradiate the laser for a predetermined time.

The operation or non-operation of the ultrasonic imaging unit 200 is determined according to the state signal (s) or control signal received from the photoacoustic imaging unit 100.

In accordance with one embodiment, if the photoacoustic imaging unit 100 is in the active state or the pre-active state, the ultrasonic imaging unit may stop operation, or may stop operation after lapse of a predetermined time or after completion of a predetermined operation. If the ultrasonic imaging unit 100 collects ultrasonic waves generated by laser, it may stop only the operation of irradiating the target object with ultrasonic waves. If the photoacoustic imaging unit 100 is in the pre-active state according to one embodiment, the ultrasonic imaging unit 200 collects ultrasonic waves generated by laser and then stops ultrasound irradiation. In this case, the ultrasonic imaging unit 200 may continuously maintain the ultrasound collection operation in at least one of the active state or the pre-active state.

In contrast, if the photoacoustic imaging unit 100 stops operation, the ultrasonic imaging unit 100 is continuously operated. That is, if the photoacoustic imaging unit 100 stops operation, the ultrasonic imaging unit 100 irradiates ultrasonic waves to the target part (t) of the target object (ob) and collects echo ultrasonic waves (r) reflected from the target part (t).

Figure 2:
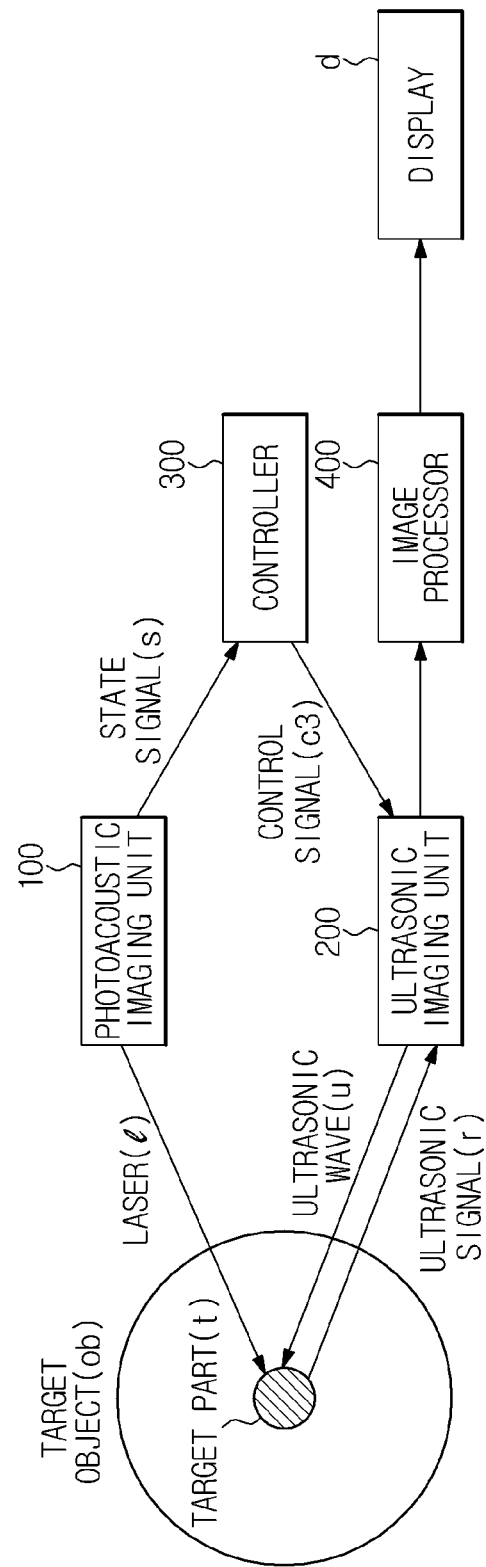
FIG. 2 is a block diagram illustrating a combined imaging apparatus according to another embodiment.

FIG. 2 is a block diagram illustrating a combined imaging apparatus according to another embodiment.

Referring to FIG. 2, the combined imaging apparatus may include two kinds of different image-data collectors, for example, a photoacoustic imaging unit 100, an ultrasonic imaging unit 200, and a controller 300 for controlling the photoacoustic imaging unit 100 and the ultrasonic imaging unit 200.

In this case, when the state signal (s) from the photoacoustic imaging unit 100 are output to the controller 300, the controller 300 reads the received state signal (s) and generates an appropriate control signal (c3) for controlling the ultrasonic imaging unit 200 in response to the received state signal (s). In accordance with one embodiment, the controller 300 may receive the state signal (s) of the photoacoustic imaging unit 100, and may transmit a control signal for adjusting a wavelength and period of laser, power on/off, etc. The controller 300 generates a control signal (c3), and transmits the control signal (c3) to the ultrasonic imaging unit 200, such that the ultrasonic imaging unit 200 may start operation or stop operation in response to the control signal (c3).

In accordance with one embodiment, the controller 300 generates a control signal capable of controlling the photoacoustic imaging unit 100 and the ultrasonic imaging unit 200, and then transmits the control signal to each of the photoacoustic imaging unit 100 and the ultrasonic imaging unit 200.

Figure 3:
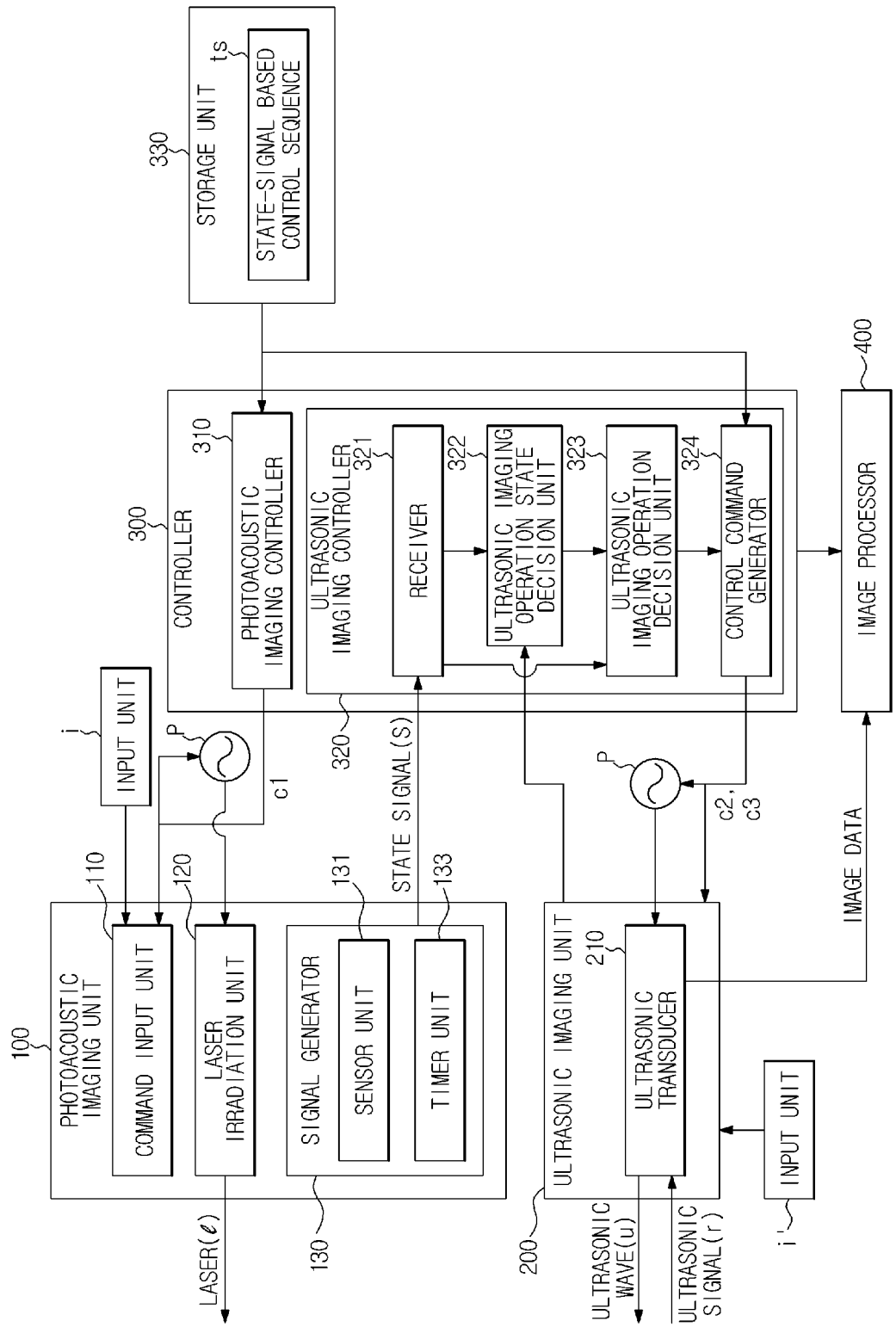
FIG. 3 is a block diagram illustrating a combined imaging apparatus according to one embodiment.

FIG. 3 is a block diagram illustrating a combined imaging apparatus according to one embodiment.

Referring to FIG. 3, the photoacoustic imaging unit 100 may include a command input unit 110, a laser irradiation unit 120, and a signal generator 130.

The command input unit 110 may receive a predetermined indication message or command for the photoacoustic imaging unit 100 from a user through a separate input unit (i), for example, a keyboard, a mouse, a trackball, a touchscreen, a paddle, etc., such that the photoacoustic imaging unit 110 is operated in response to the input indication or command. In addition, the command input unit 110 may receive a predetermined indication or command for the photoacoustic imaging unit 100 from the controller 300.

The laser irradiation unit 120 may irradiate a laser beam to the target object (ob) in response to a command from the input means (i) or the controller 310.

Figure 4:
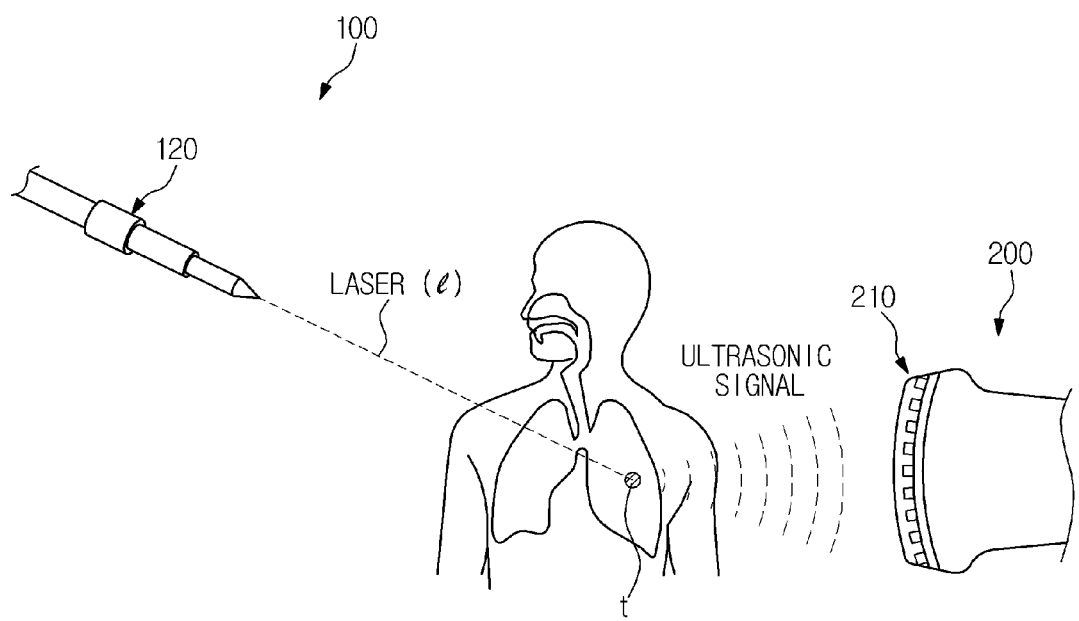
FIG. 4 is a conceptual diagram illustrating a photoacoustic imaging unit.

FIG. 4 is a conceptual diagram illustrating a photoacoustic imaging unit.

Referring to FIG. 4, after a wavelength, period, and intensity of laser are determined in response to the predetermined indication or command, if the photoacoustic imaging unit 100 receives a predetermined voltage from a power source (p) according of the determined wavelength, period, and intensity of laser, it generates a laser beam corresponding to the received voltage and outputs the laser beam to an external part. The irradiated laser arrives at the target part (t) of the target object (ob), and the target part (t) is heated so that the acoustic wave is generated. The generated acoustic waves (for example, ultrasonic signals) are collected by the ultrasonic transducer 210 of the ultrasonic imaging unit 200.

Referring to FIG. 2, the photoacoustic imaging unit 100 may generate a predetermined state signal in response to the operation state (e.g., the active state, pre-active state, or stop state) of the photoacoustic imaging unit 100 which receives a command from the command input unit 110 to generate a laser and emits the laser to an external part, and may include a signal generator 130 for transmitting the generated state signal to the ultrasonic imaging unit 200 or the controller 300.

In more detail, the signal generator 130 may include a sensor unit 131 or a timer unit 133 for sensing the operation of the photoacoustic imaging unit 100.

Figure 5A:
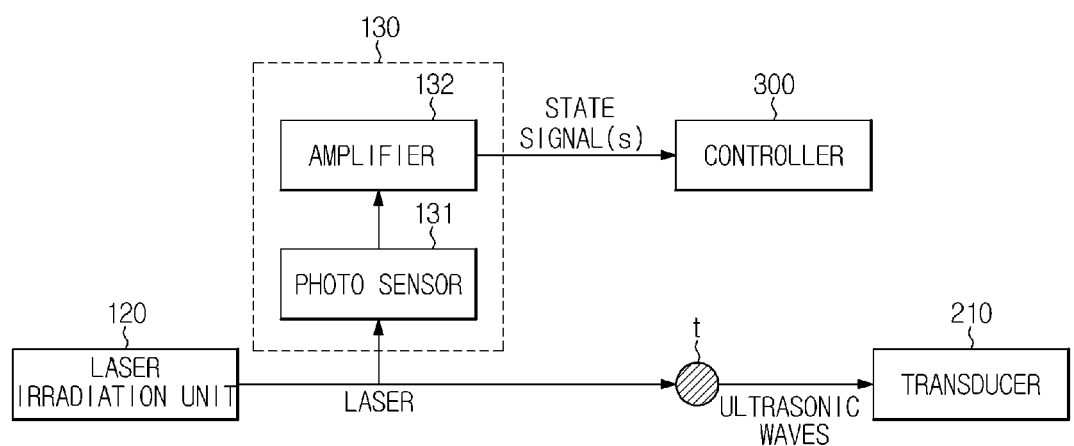
FIGS. 5A and 5B are block diagrams illustrating the photoacoustic imaging unit according to one embodiment.

FIG. 5A is a block diagram illustrating the photoacoustic imaging unit 100. Referring to FIG. 5A, the sensor unit 131 may be a photo sensor 131 (for example, a photo diode) for sensing the laser irradiated from the laser irradiation unit 120.

If the photo sensor 131 detects the laser irradiated from the laser irradiation unit 120, it generates an electric signal corresponding to the sensed laser. That is, the photo sensor 131 may generate and output the laser sensing signal. The output laser sensing signal may be transferred to the ultrasonic imaging unit 200 or the controller 300. If necessary, the signal generator 130 may further include an amplifier 132 for amplifying the laser sensing signal output by the photo sensor 131.

If the laser beam is detected by the photo sensor 131 and the photo sensor 131 outputs the laser sensing signal, this means that the laser irradiation unit 120 emits the laser beam, such that the laser sensing signal indicates that the photoacoustic imaging unit 100 is currently operating. That is, the laser sensing signal indicates that the photoacoustic imaging unit 100 is in the active state.

Figure 5B:
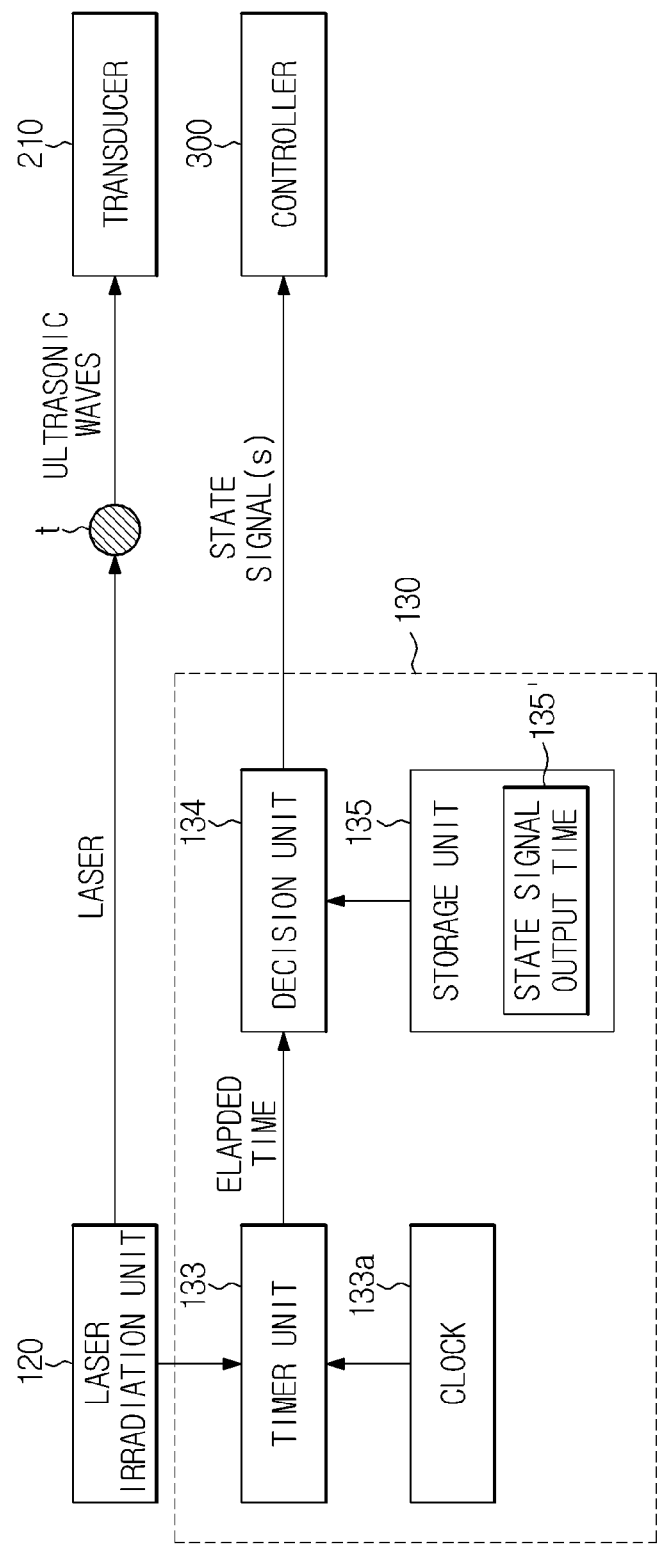

FIG. 5B is a block diagram illustrating the photoacoustic imaging unit according to another embodiment.

Referring to FIG. 5B, the signal generator 130 may include the timer unit 133. The signal generator 130 may further include the timer unit 133 for measuring a time elapsed after the laser beam is irradiated from the laser irradiation unit 120. The timer unit 133 may receive time data from the clock 133a so as to measure the elapsed time.

If the timer unit 133 measures the elapsed time, the decision unit 134 determines whether the elapsed time measured on the basis of not only an output time 135' of at least one state signal stored in a separate storage unit 135 but also the measured elapsed time is identical to or longer than at least one state signal output time. If the measured elapsed time is identical to or longer than at least one state signal output time, the timer unit 133 may generate a state signal corresponding to the at least one state signal output time and output the same to the controller 300.

In more detail, the state signal output time 135' is pre-entered by the user or the like so as to determine a current state of the photoacoustic imaging unit 100.

The state signal output time 135' may include an active-state signal output time for deciding the active state, or may include a pre-active state signal output time for deciding the pre-active state.

In more detail, for laser re-irradiation after the laser irradiation unit 120 irradiates the laser beam, a predetermined time elapses. In this case, the state signal output time 135' may be decided using an average time required for re-irradiation. In order to prevent the photoacoustic imaging unit 100 and the ultrasonic imaging unit 200 from being simultaneously operated, a standard deviation is deducted from the average time required for re-irradiation, and the average time from which the standard deviation is deducted may be used as the active-state signal output time. In addition, a predetermined time is deducted from the active-state signal output time, such that the deducted result may be used as a pre-active active signal output time. That is, the pre-active state signal output time may be shorter than the active-state signal output time.

Therefore, after lapse of a predetermined time (i.e., a state signal output time), the signal generator 130 may output at least one state signal (e.g., an active state signal and a pre-active state signal) indicating a current state of the photoacoustic imaging unit 100.

In accordance with one embodiment of the photoacoustic imaging unit 100, if the photoacoustic imaging unit 100 does not operate, i.e., if the photoacoustic imaging unit 100 is not in the active state or the pre-active state, the signal generator 130 may generate no signal as necessary. That is, the photoacoustic imaging unit 100 generates a necessary signal only in the active state or in the pre-active state, and transmits the signal to an ultrasonic imaging controller 320, such that the ultrasonic imaging unit 200 can be controlled.

Figure 6A:
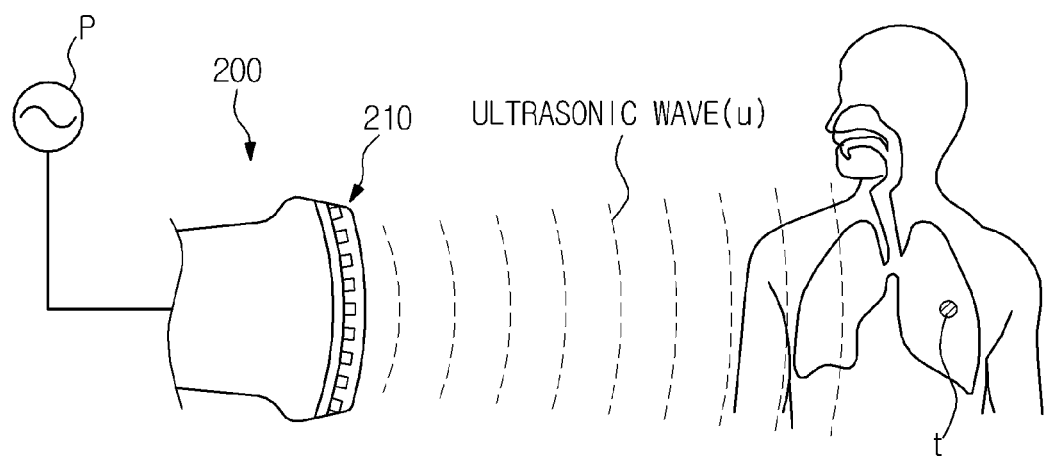
FIGS. 6A and 6B are block diagrams illustrating an ultrasonic imaging unit according to one embodiment.
Figure 6B:
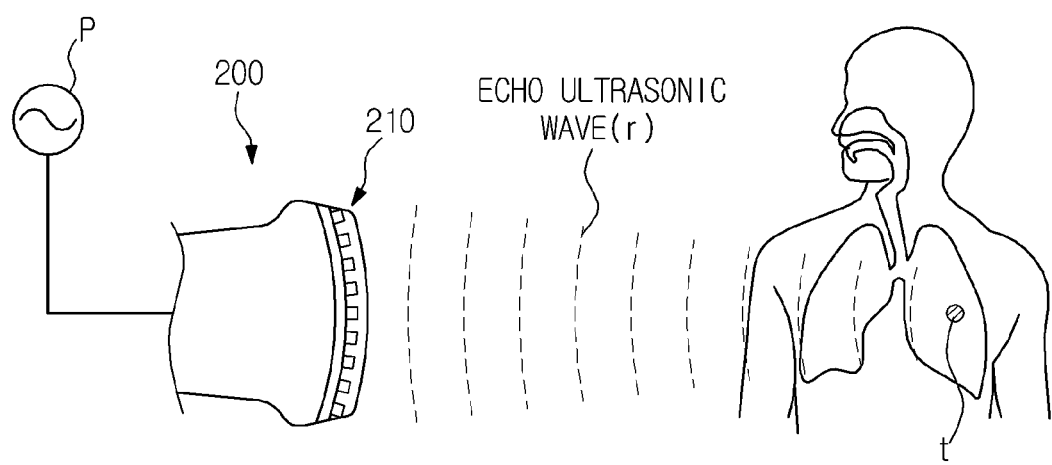
Figure 7:
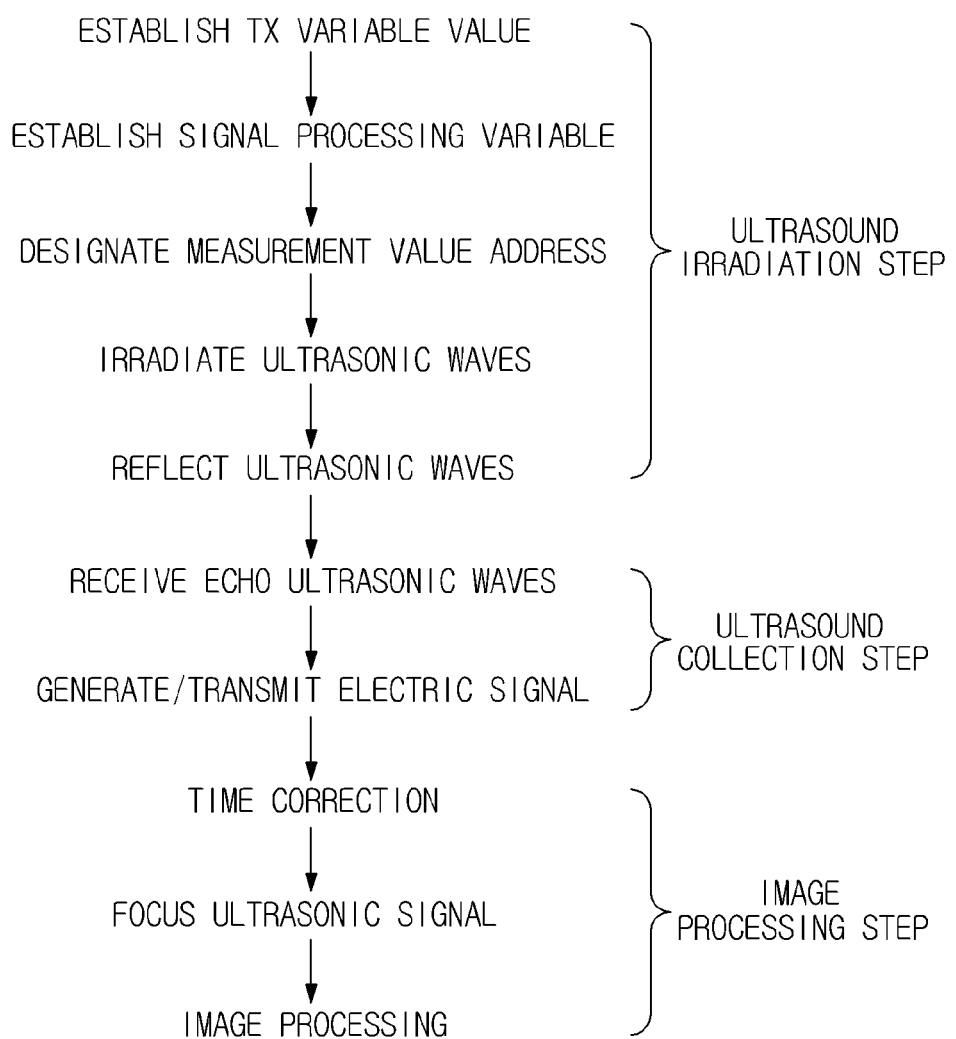
FIG. 7 is a flowchart illustrating various operations of the ultrasonic imaging unit.

Referring to FIG. 3, the ultrasonic imaging unit 200 may include an ultrasonic transducer 210. FIGS. 6A and 6B are block diagrams illustrating the ultrasonic imaging unit according to one embodiment. FIG. 7 is a flowchart illustrating various operations of the ultrasonic imaging unit.

The ultrasonic imaging unit 200 generates ultrasonic waves, irradiates the ultrasonic waves to the target part (t), and collects the ultrasonic waves reflected from the target part (t). For image processing on the basis of the collected ultrasonic waves, the ultrasonic imaging unit 200 may perform an ultrasonic irradiation operation, an ultrasound reception operation, and an image processing operation as shown in FIG. 7. In this case, the image processing step may be carried out by a separate information processing unit connected to the ultrasonic imaging unit 200. For example, the image processing operation may be carried out by a main body of an ultrasonic diagnosis unit coupled with the ultrasonic probe.

Referring to the ultrasonic irradiation operation, a Tx variable value for ultrasound irradiation may be established in a manner that the ultrasonic imaging unit 100 irradiates ultrasonic waves to the target part (t), and a signal processing variable for signal processing may be established, such that an address in which a measurement value of the target part (t) to which ultrasonic waves are to be irradiated will be temporarily or non-temporarily stored is designated.

As can be seen from FIG. 6A, the ultrasonic transducer 210 installed at some parts of the ultrasonic probe of the ultrasonic imaging unit 200 may receive an AC current from the power source (p), and the ultrasonic transducer 110 vibrates by the AC current so that the ultrasonic waves are generated and emitted to the external part. The generated ultrasonic waves (u) are irradiated to the target part (t).

Referring to FIG. 6B, the ultrasonic waves (u) irradiated from the ultrasonic imaging unit 200 are reflected from the target part (t).

Referring to the ultrasonic collection step shown in FIG. 7, the ultrasonic transducer 100 of the ultrasonic imaging unit 100 receives the echo ultrasonic waves reflected from the target part (t). The ultrasonic transducer 110 may generate an AC current of a frequency corresponding to a frequency of the received echo ultrasonic waves. That is, the ultrasonic transducer 110 may generate an ultrasonic image signal. The generated ultrasonic image signal may be transferred to the separate information processing device for generating an ultrasonic image. In this case, before the ultrasonic image signal is transferred to the information processing device, the ultrasonic image signal may be temporarily or permanently stored in a separate storage space.

In contrast, due to a distance difference between each channel of the ultrasonic transducer 110 of the ultrasonic probe and the target part, there may be a slight time difference between ultrasonic waves which have been generated or reflected from the same target part (t) and applied to the ultrasonic transducer 110. Therefore, a method for delaying propagation of a specific signal from among ultrasonic image signals received from individual channels may compensate for a time of the ultrasonic image signal, such that ultrasonic signals generated at the same time may be focused.

In addition, if ultrasonic image signals of a plurality of time-compensated channels are focused, an ultrasonic image corresponding to the received ultrasonic waves may be generated using a conversion function such as a point spread function as necessary.

Thereafter, brightness, contrast, and color may be corrected, or predetermined image processing for generating a three-dimensional (3D) image using a plurality of ultrasonic images may be applied to the generated ultrasonic image, such that the complete ultrasonic image can be obtained.

In accordance with one embodiment of the ultrasonic imaging unit 200, the ultrasonic imaging unit 200 may collect the ultrasonic waves generated from the target part (t) in response to the laser emitted from the photoacoustic imaging unit 100. In this case, the ultrasound reception step and the image processing step may be carried out by the ultrasonic imaging unit 100 as described above.

In accordance with one embodiment, the ultrasonic imaging unit 200 may receive a predetermined indication or command from an external user through a separate input means (i') such as a keyboard, a mouse, a trackball, a touchscreen, etc., such that the ultrasonic imaging unit 200 may be operated in response to the predetermined indication or command.

Referring to FIG. 3, the controller 300 may include the photoacoustic imaging controller 310 and the ultrasonic imaging controller 320.

In accordance with one embodiment, the controller 300 may includes the photoacoustic imaging controller 310 and the ultrasonic imaging controller 320, which operate on the basis of state signals according to a predetermined sequence (i.e., a control sequence (ts) based on a state signal) designed in the controller 300. The controller 300 may determine an operation state according to a state signal and a control signal, and may control the photoacoustic imaging unit 100 and the ultrasonic imaging unit 200.

In accordance with one embodiment, the controller 300 may call a predetermined sequence from the separate storage unit 330.

The state-signal based control sequence (ts) may be, for example, a sequence for determining a state or operation of the ultrasonic imaging unit 200 in response to a state signal from the photoacoustic imaging unit 100. The ultrasonic imaging unit 200 may stop a predetermined operation (for example, ultrasound irradiation) in response to a state or operation decided by the state-signal based control sequence (ts). The ultrasonic imaging unit 100 performs various combined image measurement operations on the basis of a state signal. For example, the combined image measurement operations may include an operation for generating a control signal of the ultrasonic imaging unit 200 to collect ultrasonic signals generated by the photoacoustic imaging unit 100, and an operation for establishing a variable for ultrasound processing. Examples of the state-signal based control sequence (ts) are shown in FIG. 10C, and a detailed description thereof will be given later.

The photoacoustic imaging controller 310 and the ultrasonic imaging unit 320 of the controller 300 may generate a state-signal based control command of the ultrasonic imaging unit 200 according to the state-signal based control sequence (ts), and transmit the generated control command to the ultrasonic imaging unit 200.

The photoacoustic imaging controller 310 transmits a control command (c1) to the command input unit 110 of the photoacoustic imaging unit 100 in such a manner that the photoacoustic imaging unit 100 is operated in response to the control command (c1). For example, the photoacoustic imaging unit emits a laser beam to the target object (ob) in response to a control command (c1) of the photoacoustic imaging controller 310, such that the laser beam is irradiated to the target object (ob). In accordance with one embodiment, the photoacoustic imaging controller 310 generates the control command (c1) for the power source (p), and controls application of a current to the laser irradiation unit 120 by the power source (p), such that it may control the operation (i.e., laser irradiation) of the photoacoustic imaging unit 100.

The ultrasonic imaging controller 320 generates a control command of the ultrasonic imaging unit 200, transmits the control command to the ultrasonic imaging unit 200, and controls the ultrasonic imaging unit 200 configured to irradiate ultrasonic waves to the target object. In this case, the ultrasonic imaging controller 320 controls the power source (p) electrically connected to the ultrasonic transducer 210, such that it may control ultrasound irradiation of the ultrasonic imaging unit 200.

In this case, the ultrasonic imaging controller 320 may further include a receiver 321, an ultrasonic imaging operation state decision unit 322, an ultrasonic imaging operation decision unit 323, and a control command generation unit 324.

The receiver 321 may receive signals from the photoacoustic imaging unit 100. In this case, signals received by the receiver 321 may be state signals indicating the operation state of the photoacoustic imaging unit 100, and may be generated by the signal generator 130 of the photoacoustic imaging unit 100. The signals received by the receiver 321 are transferred to the ultrasonic imaging operation state decision unit 322 or the ultrasonic imaging operation decision unit 323.

The ultrasonic imaging operation state decision unit 322 may decide the operation state of the ultrasonic imaging unit 200 when the receiver 321 receives the output signal of the photoacoustic imaging unit 100. As stated in FIG. 7, the state of the ultrasonic imaging unit 200 may be broadly classified into the ultrasound irradiation state, the ultrasound collection state, and the image processing state. The ultrasonic imaging operation state decision unit 322 receives a predetermined signal through the ultrasonic imaging unit 200, such that it can determine a current state of the ultrasonic imaging unit 200. The decision result is transferred to the ultrasonic imaging operation decision unit 323.

In accordance with one embodiment, the ultrasonic imaging operation decision unit 323 may determine the operation of the ultrasonic imaging unit 200 according to the operation state of the photoacoustic imaging unit 100. Here, the operation state of the photoacoustic imaging unit 100 is received by the receiver 321. In this case, if the receiver 321 receives no signal from the photoacoustic imaging unit 100, the ultrasonic imaging operation decision unit 323 determines the stop state of the photoacoustic imaging unit 100 such that it may be possible to determine the operation state of the ultrasonic imaging unit 200.

The ultrasonic imaging operation decision unit 323 may determine the operation state of the ultrasonic imaging unit 200 using the operation state of the photoacoustic imaging unit 100 and the operation state of the ultrasonic imaging operation state decision unit 322. Here, the operation state of the photoacoustic imaging unit 100 is received by the receiver 321, and the operation state of the ultrasonic imaging unit 200 may be decided by the ultrasonic imaging operation state decision unit 322.

In this case, the operation of the ultrasonic imaging unit 200 may be stoppage of the operation of the ultrasonic imaging unit 200 or may be maintenance of the operation of the ultrasonic imaging unit 200. In accordance with one embodiment, the ultrasonic imaging operation decision unit 323 may determine the number of additional operations of the ultrasonic imaging unit 200, such that the ultrasonic imaging unit 200 may be operated according to the decided number of additional operations. That is, assuming that the ultrasonic imaging unit 200 has to stop operation or continuously operates, the ultrasonic imaging unit 100 may further operate once or twice and then stop operation.

FIG. 8A is a table illustrating the operation states of the ultrasonic imaging unit according to an operation state of the photoacoustic imaging unit.

The ultrasonic imaging operation decision unit 32 may decide the operation state of the ultrasonic imaging unit 200 according to the operation state of the photoacoustic imaging unit 100. In this case, the operation state of the photoacoustic imaging unit 100 may be any one of the stop state, the active state, and the pre-active state as shown in FIG. 8A.

If the photoacoustic imaging unit 100 is in the stop state, the ultrasonic imaging operation decision unit 323 may decide to operate the ultrasonic imaging unit 200 (See the first column of FIG. 8A).

If the photoacoustic imaging unit 100 is in the active state, the ultrasonic imaging operation decision unit 323 may decide to stop the ultrasonic imaging unit 200 as shown in FIG. 8A (See the second column of FIG. 8A). As described above, the number of additional ultrasound irradiation operation times of the ultrasonic imaging unit 200 is also decided by the ultrasound imaging operation decision unit 323, such that the ultrasonic imaging unit 200 may be further operated the decided number of ultrasound irradiation operation times, and may stop the ultrasound irradiation operation.

However, the stop operation by the ultrasonic imaging unit 200 indicates that the image generation process in which ultrasonic waves are irradiated and echo ultrasonic waves are received so as to generate an image has been stopped. In the case of the embodiment in which the ultrasonic imaging unit 200 receives ultrasonic waves generated from the target part (t) according to laser irradiation of the photoacoustic imaging unit 100, the stop operation by the ultrasonic imaging unit 200 does not stop the operation for collecting the generated ultrasonic waves according to laser irradiation and the operation of generating an associated image.

If the photoacoustic imaging unit 100 is in the pre-active state, the ultrasonic imaging operation decision unit 323 may allow the ultrasonic imaging unit 20 to stop operation in the same manner as in the above-mentioned active state case (See the third column of FIG. 8A). As shown in the fourth column of FIG. 8A, the ultrasonic imaging unit 200 may be ready to stop operation. If the ultrasonic imaging unit 200 is ready to stop operation, the ultrasonic imaging unit 200 may stop operation either after lapse of a predetermined number of times or after lapse of a predetermined number of measurement times entered by a user or the like. In addition, the ultrasonic imaging unit 200 may also be operated the decided number of additional operations of the ultrasonic imaging unit 200. The decided number of additional operations of the ultrasonic imaging unit 200 may be decided on the basis of a time between the pre-active state and the active state.

FIG. 8B is a table illustrating the operation states of the ultrasonic imaging unit according to the operation states of the photoacoustic imaging unit and the ultrasonic imaging unit. FIGS. 9A and 9B are flowcharts illustrating the case in which a state signal is input during operation of the ultrasonic imaging unit.

Meanwhile, the ultrasonic imaging operation decision unit 323 according to another embodiment may decide to operate the ultrasonic imaging unit 200 on the basis of the operation states of the photoacoustic imaging unit 100 and the ultrasonic imaging unit 200.

If the photoacoustic imaging unit 100 is in the stop state, the ultrasonic imaging operation decision unit 323 may decide to operate the ultrasonic imaging unit 200 as shown in FIG. 8B (See the first column of FIG. 8B). The above-mentioned description is identical to those of the case in which the operation of the ultrasonic imaging unit 200 is decided according to the operation state of the photoacoustic imaging unit 100.

If the photoacoustic imaging unit 100 is in the active state or the pre-active state, the ultrasonic imaging operation decision unit 323 first confirms the operation state of the ultrasonic imaging unit 200 as shown in FIG. 8B, such that it decides the operation of the ultrasonic imaging unit 200 (See the second and third columns of FIG. 8A).

Under the condition that the receiver 321 receives the state signal from the photoacoustic imaging unit 100 when the ultrasonic imaging unit 200 is in the ultrasonic irradiation step as shown in FIG. 9A, if the state signal of the received photoacoustic imaging unit 100 is an active state signal or a pre-active state signal, the ultrasonic imaging operation decision unit 323 may decide to stop operating the ultrasonic imaging unit (See third and fifth columns of FIG. 8B).

If the receiver 321 receives the state signal from the photoacoustic imaging unit 100 when the ultrasonic imaging unit 200 is in the ultrasonic reception step or in the ultrasonic image processing step as shown in FIG. 9B, the ultrasonic imaging operation decision unit 323 decides to maintain the operation of the ultrasonic imaging unit 200 (See the second and fourth columns of FIG. 8B). In this case, the ultrasonic imaging unit 200 may stop ultrasound irradination when the operation for collecting ultrasonic waves is ended or after the image processing state is ended. In accordance with one embodiment, the ultrasonic imaging unit 200 maintains a current operation only when the photoacoustic imaging unit 100 read from the state signal of the photoacoustic imaging unit 100 is in the pre-active state. The ultrasonic imaging unit 200 stops operation irrespective of the current state of the ultrasonic imaging unit 200 when the photoacoustic imaging unit 100 is in the active state.

If the operation of the ultrasonic imaging unit 200 is decided by the ultrasonic imaging operation decision unit 323, the control command generation unit 324 generates control commands (c2, c3) according to the ultrasonic imaging unit 200's operation state decided by the ultrasonic imaging operation decision unit 323, and transmits current to either the ultrasonic imaging unit 200 or the power source (p) for supplying the current to the ultrasonic imaging unit 200. The operation of the ultrasonic imaging unit 200 may be stopped or maintained according to the control command (c2) received from the ultrasonic imaging unit 200. For example, the power source (p) stops the supply of current to the ultrasonic imaging unit 200 (e.g., the transducer 210) according to the received control command (c3), and stops ultrasound generation.

As described above, the controller 300 receives the state signal from the photoacoustic imaging unit 100 in real time, generates a control command of the ultrasonic imaging unit 200 using the received state signal, and controls the ultrasonic imaging unit 200 according to the operation of the photoacoustic imaging unit 100. In conclusion, the controller 300 may stop or minimize generation of image distortion caused by operation collision between the photoacoustic imaging unit 100 and the ultrasonic imaging unit 200.

Figure 10A:
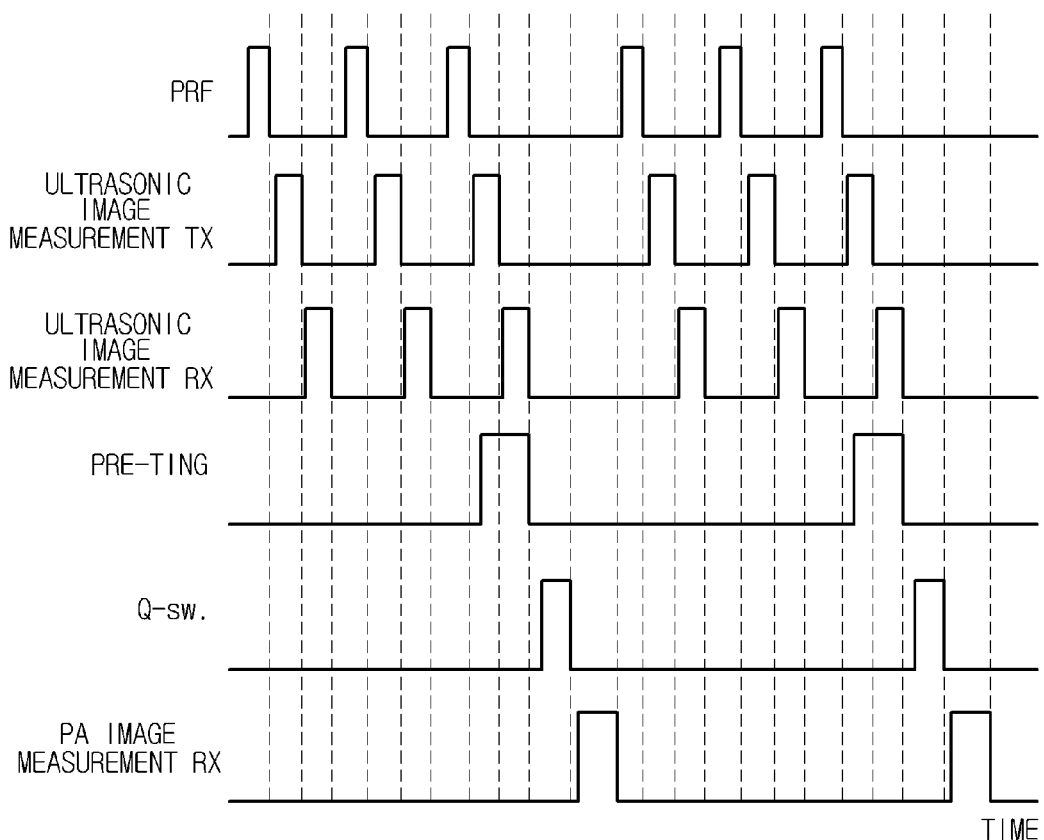
FIGS. 10A to 10C are waveform diagrams illustrating the operations of the ultrasonic imaging unit and the photoacoustic imaging unit.
Figure 10B:
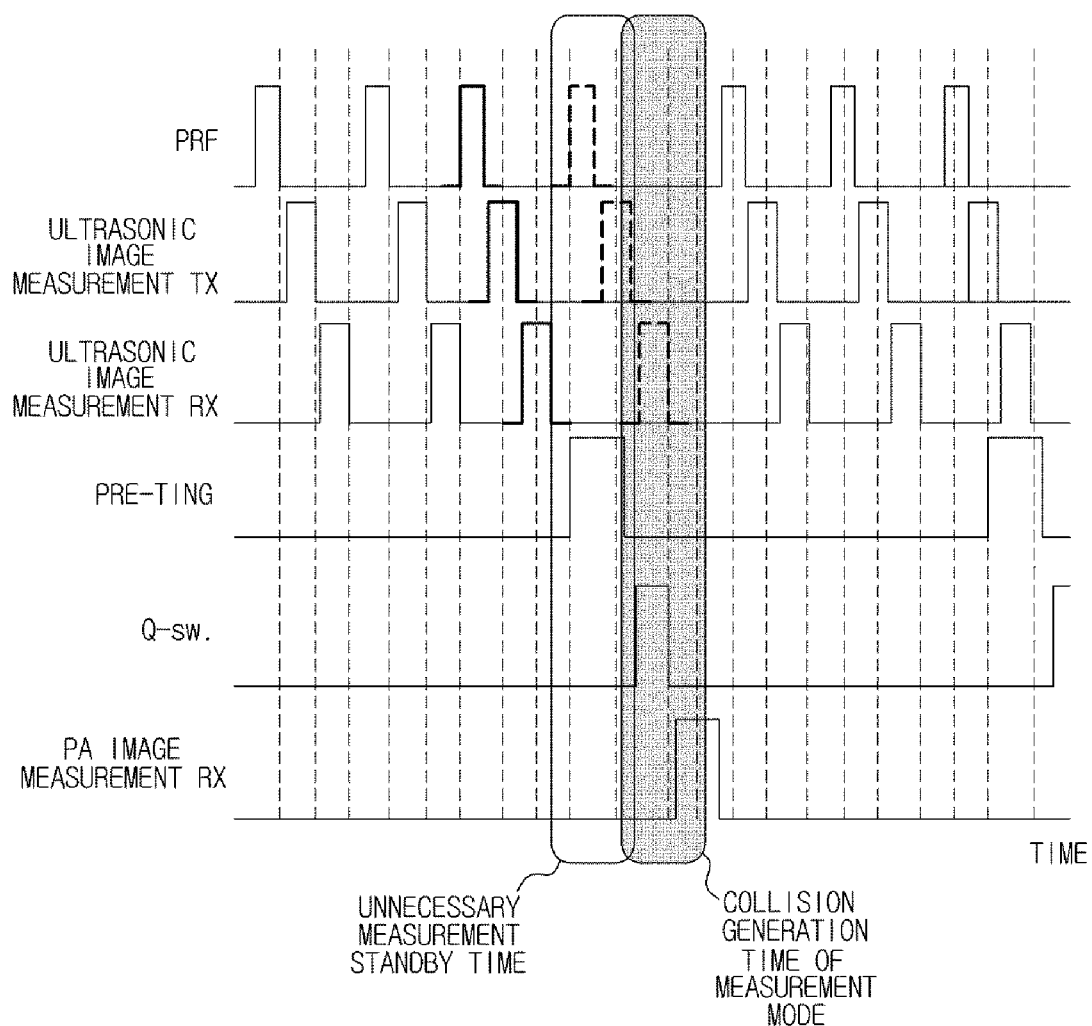
Figure 10C:
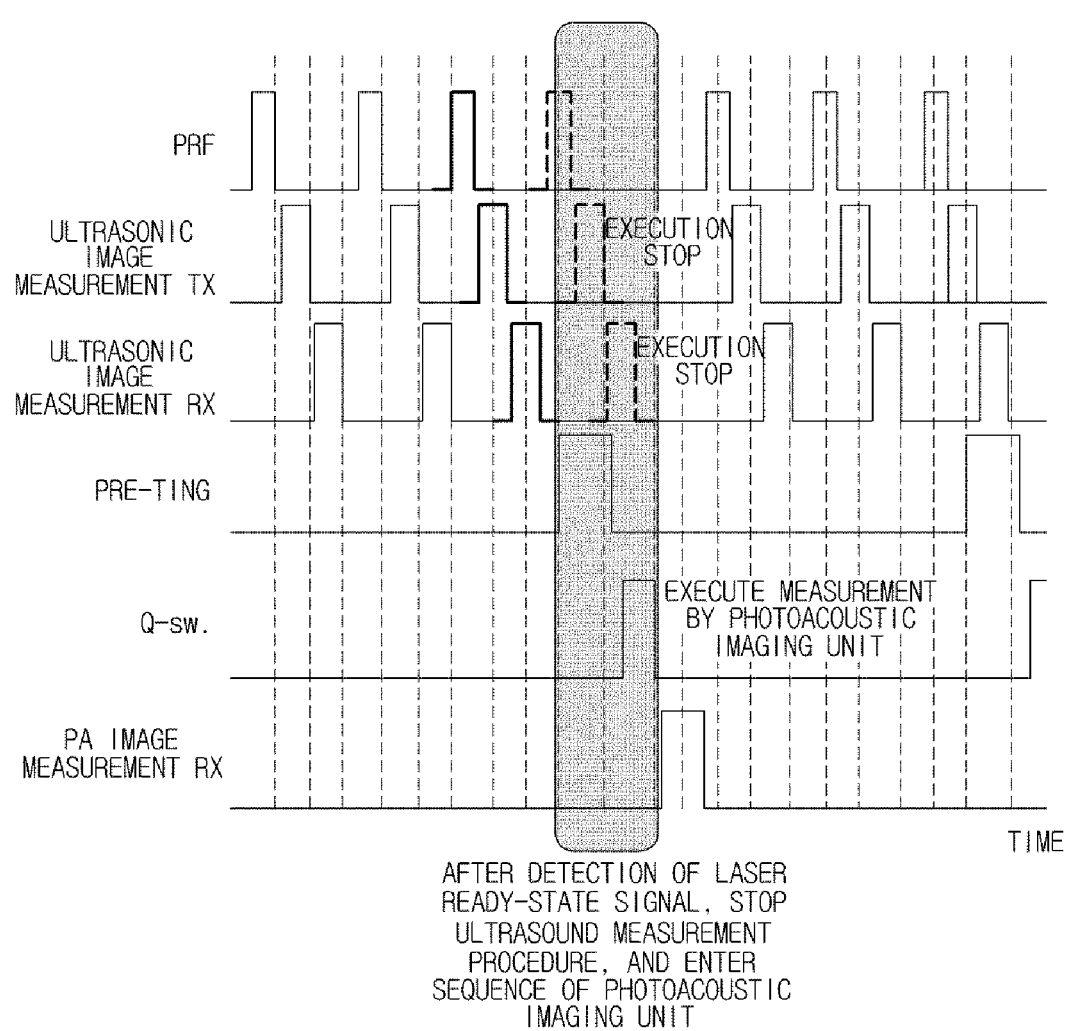

FIGS. 10A to 10C are waveform diagrams illustrating the operations of the ultrasonic imaging unit 200 and the photoacoustic imaging unit 100 of the combined imaging unit.

In FIGS. 10A to 10C, a rectangle may indicate an operation state, and the remaining parts including no rectangle may indicate an idle state or a stop or halt state. In addition, the first column shown in FIGS. 10A to 10C may indicate a ready state for ultrasound irradiation by the ultrasonic imaging unit 200, the second column may indicate an ultrasound irradiation state caused by the ultrasonic imaging unit 200, and the third column may indicate an echo ultrasound reception state. In addition, the fourth column shown in FIGS. 10A to 10C may indicate a ready state of laser irradiation of the photoacoustic imaging unit 100. That is, the fourth column of FIGS. 10A to 10C may indicate a pre-active state or other states located before the pre-active state. The fifth column may indicate an operation state of a Q switch, i.e., the fifth column indicates a laser irradiation state (i.e., an active state), and the sixth column (PA image measurement RX) may indicate a state for collecting ultrasonic waves generated by laser.

As can be seen from FIGS. 10A to 10C, the photoacoustic imaging unit 100 may not continuously irradiate the laser. After the laser is irradiated once, a predetermined time for laser irradiation is needed (See the time interval between the fourth column and the fifth column of FIGS. 10A to 10C). Therefore, the photoacoustic imaging unit 100 irradiates an energy beam, i.e., laser beam (I), to the target part (t) at intervals of a predetermined time. In this case, the laser irradiation period may be 10~20 Hz.

FIG. 10A is a timing diagram illustrating a method for ideally acquiring an ultrasonic image of a target object by a combined imaging apparatus. Referring to FIG. 10A, the combined imaging apparatus can be controlled in response to a time schedule control sequence based on a measurement time, irrespective of a state signal of the photoacoustic imaging unit 100, under the condition that the laser output period and each measurement time are always ideal. In accordance with the time schedule control sequence as shown in FIG. 10A, the ultrasonic imaging unit 200 performs ultrasound irradiation a predetermined number of times (for example, three times) in the middle of an ultrasonic image acquisition time caused by laser emission of the photoacoustic imaging unit 100, such that it can acquire an ultrasonic image.

However, the laser irradiation period by the photoacoustic imaging unit 100 may be slightly unstable and be variable, because of not only a laser temperature and a condition of laser before irradiated of the photoacoustic imaging unit 100 but also the jitter problem of the Q switch. Therefore, the laser irradiation period may be changed from several millimeters to several tens of seconds. That is, the photoacoustic imaging unit 100 may not operate at a correct time, and may have a predetermined error in the operation time.

In addition, the ultrasonic imaging unit 200 may have an irregular-, longer-, or shorter-ultrasound measurement time according to the number of received ultrasound sampling times, measurement depth, and processor load. Therefore, efficiency of image acquisition or quality of the acquired image may be deteriorated. For example, the operation of the ultrasonic imaging unit 200 may be ended at an early stage or the laser irradiation operation of the photoacoustic imaging unit 100 is delayed, such that a measurement standby time is unnecessarily elongated as shown in FIG. 10B, resulting in deterioration of image acquisition efficiency. In contrast, if the ultrasound collection operation of the ultrasonic imaging unit 200 may be delayed or the standby time of the photoacoustic imaging unit 100 is reduced, the photoacoustic imaging unit 100 and the ultrasonic imaging unit 200 may simultaneously irradiate a laser beam or ultrasonic waves to a target object as shown in FIG. 10B. Those may result in unexpected collision between measurement modes of the combined imaging apparatus. If the collision occurs by simultaneous operation of the photoacoustic imaging unit 100 and the ultrasonic imaging unit 200, the generated image may include an image distortion not physically present in the original image and the image quality will be deteriorated with a high possibility.

In contrast, when the combined imaging apparatus is controlled using a control sequence based on a state signal of the photoacoustic imaging unit 100, a collision between the photoacoustic imaging unit 100 and the ultrasonic imaging unit 200 is prevented from occurring as shown in FIG. 9C, such that image acquisition efficiency can be improved and the image quality can be prevented from being deteriorated.

In more detail, as can be seen from FIG. 9C, the combined imaging apparatus stops the operation of the ultrasonic imaging unit 200 (i.e., ultrasound irradiation operation) in response to an operation state of the photoacoustic imaging unit 100, such that laser irradiation of the photoacoustic imaging unit 100 and ultrasound irradiation of the ultrasonic imaging unit 200 are not simultaneously performed.

As a result, operation collision may not occur between the photoacoustic imaging unit 100 and the ultrasonic imaging unit 200 as shown in FIG. 10B. In more detail, the ultrasonic imaging unit 200 is controlled in response to a state of the photoacoustic imaging unit 100, such that the photoacoustic imaging unit 100 and the ultrasonic imaging unit 200 are prevented from being simultaneously operated. As a result, image distortion caused by collision of measurement modes can be prevented from occurring or can be removed in advance.

In addition, the ultrasonic imaging unit 200 continuously performs the ultrasound irradiation and the collection of echo-ultrasonic waves until the stop command (c3) of the ultrasound operation is received in response to a separate signal (for example, a state signal), such that it can prevent an unnecessary measurement standby time from being generated.

Figure 11:
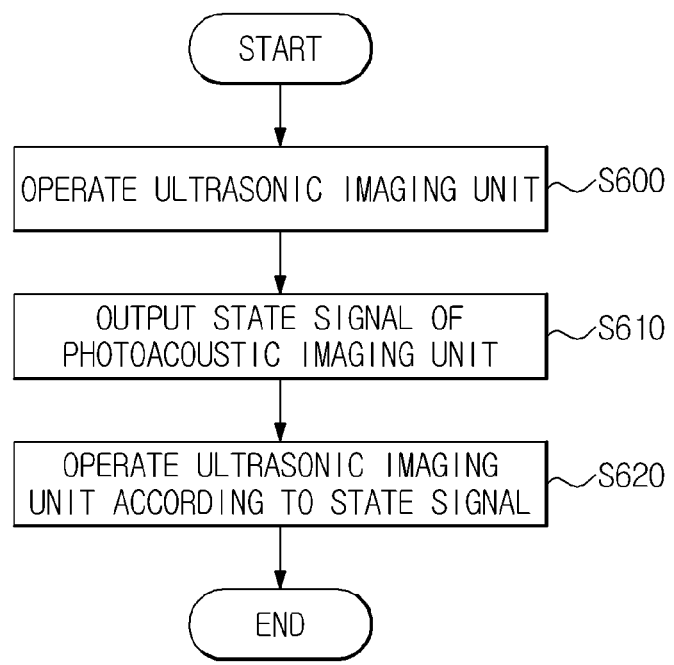
FIGS. 11 to 13 are flowcharts illustrating a method for controlling the combined imaging apparatus.
Figure 12:
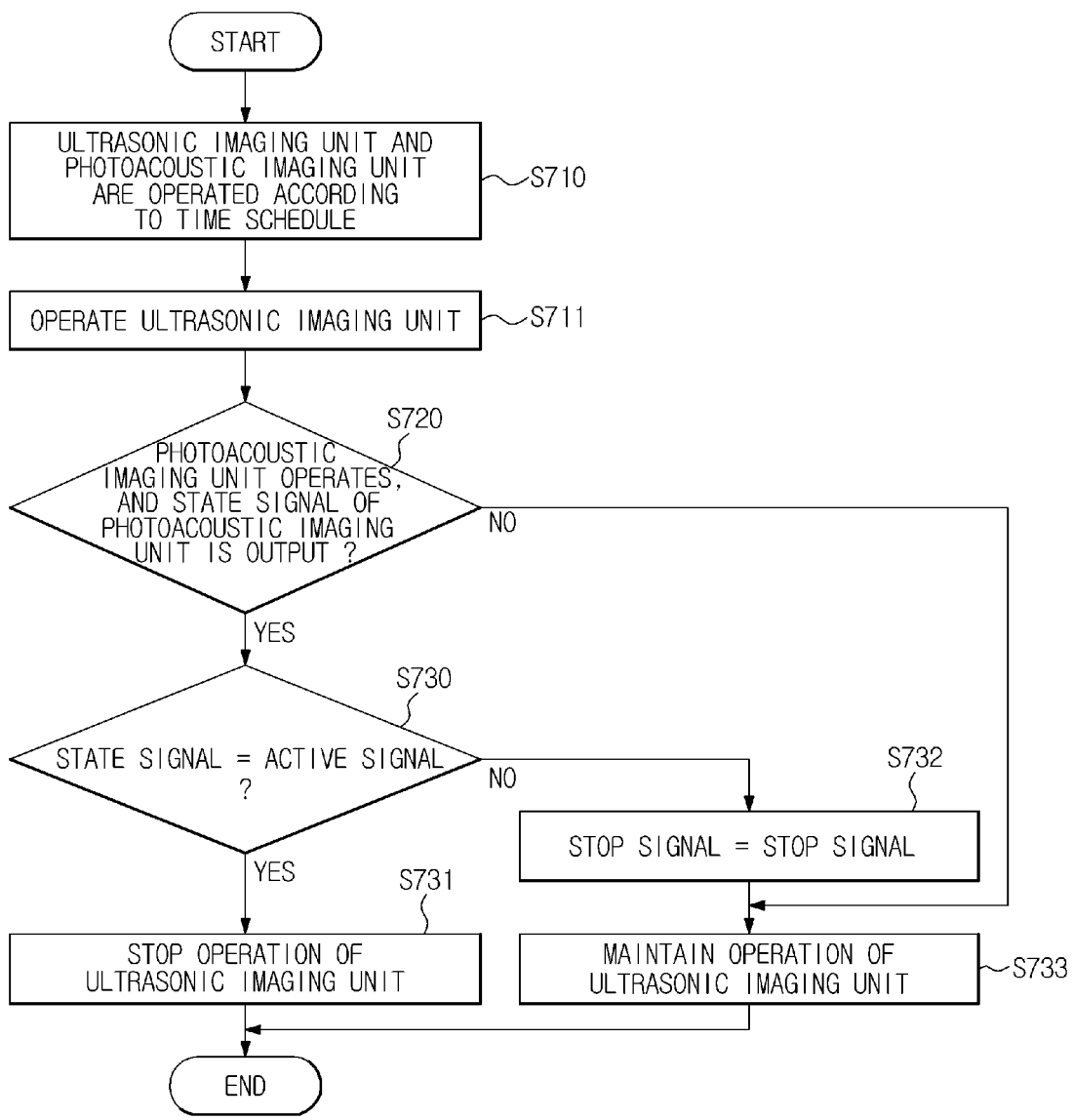
Figure 13:
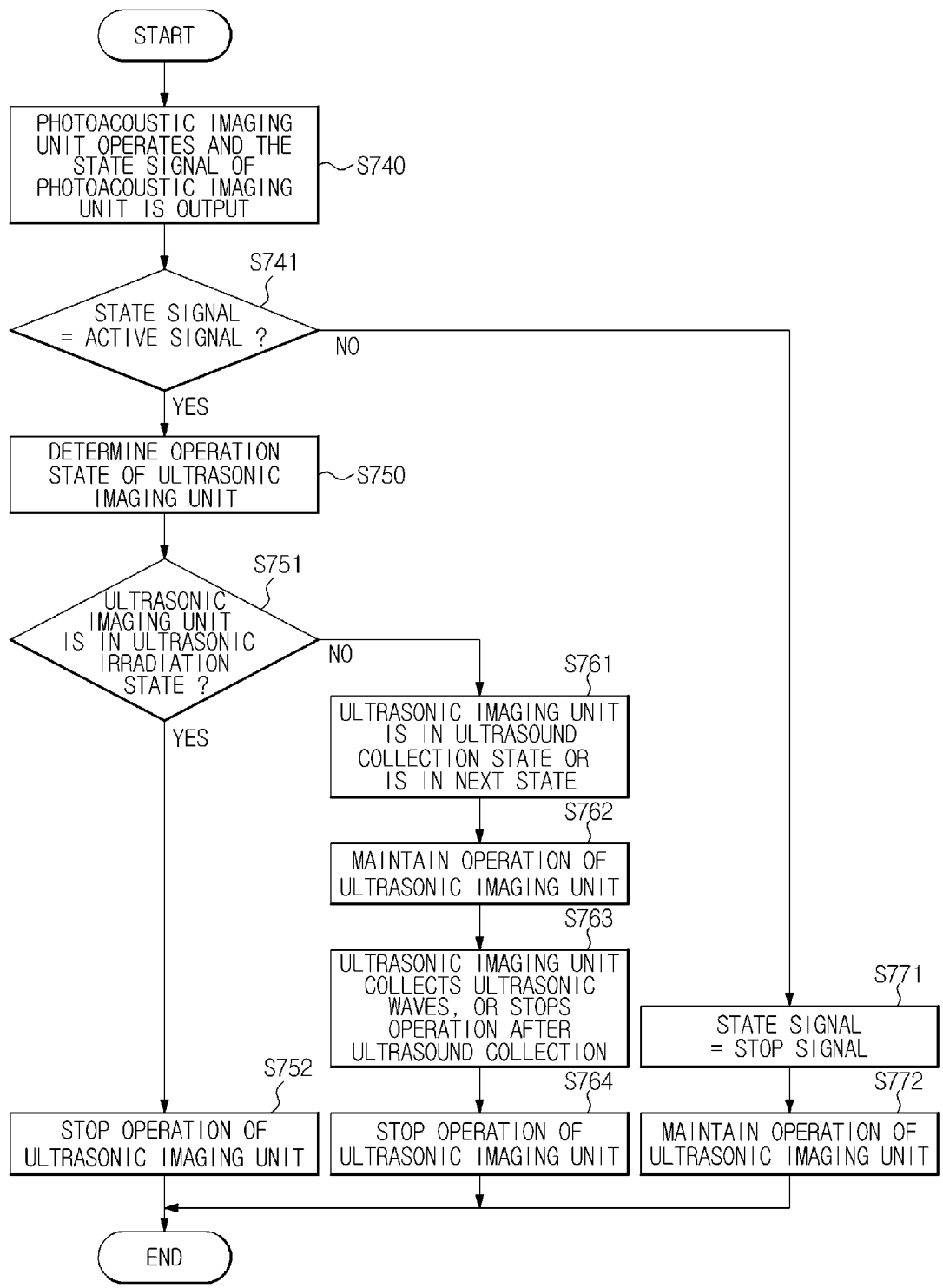

FIGS. 11 to 13 are flowcharts illustrating a method for controlling the combined imaging apparatus according to one embodiment.

Referring to FIG. 11, according to the method for controlling the combined imaging apparatus, the ultrasonic imaging unit 200 may operate in step 610. In this case, the ultrasonic imaging unit 200 may operate in response to the state-signal based control sequence (ts).

For example, assuming that the photoacoustic imaging unit 100 starts operation according to the state-signal based control sequence (ts), a state signal indicating the operation state of the photoacoustic imaging unit 100 may be output in step 610 when the sensor unit 131 detects the operation of the photoacoustic imaging unit 100 or when the time unit 133 measures an elapsed time. In this case, the photoacoustic imaging unit 100 may be an active state, a pre-active state, or a stop state. The state signal may indicate any one of the active state, the pre-active state, or the stop state. Of course, in accordance with another embodiment, a separate signal for the stop state may not be generated.

The ultrasonic imaging unit 200 may be operated in response to a state signal which is directly received from the photoacoustic imaging unit 100 or is received through the controller 300, or may also be operated in response to a control command based on the state signal in step 620.

Referring to a detailed method for controlling the combined imaging apparatus as shown in FIG. 12, the ultrasonic imaging unit 200 and the photoacoustic imaging unit 100 are operated in response to the state-signal based control sequence (ts) in step 710. For example, the ultrasonic imaging unit 200 and the photoacoustic imaging unit 100 may be continuously operated according to the state-signal based control sequence (ts) as shown in FIG. 10A.

Meanwhile, if the ultrasonic imaging unit 200 is operated in response to the control sequence in step 711, the state signal indicating a current state of the photoacoustic imaging unit 100 may be generated and output in step 720. If the state signal indicates the active state or the pre-active state in step 730, i.e., if the photoacoustic imaging unit 100 is operated in such a manner that the operation of the photoacoustic imaging unit 100 overlaps the operation of the ultrasonic imaging unit 200 (See FIG. 10B), the ultrasonic imaging unit 200 stops operation in response to the state signal in step 731 (See FIG. 10C). In accordance with one embodiment, the controller 300 receives a state signal indicating the active state or pre-active state, generates a control signal capable of controlling the ultrasonic imaging unit 200 on the basis of the received state signal, and transmits the control signal to the ultrasonic imaging unit 200, such that the ultrasonic imaging unit 200 may stop operation.

If the state signal is a stop signal in step 732, the ultrasonic imaging unit 200 or the controller 300 determines that the photoacoustic imaging unit 100 does not operate yet, the ultrasonic imaging unit 200 irradiates ultrasonic waves, and collects echo ultrasonic waves, such that it may continuously generate an ultrasonic image in step 733.

Of course, if the photoacoustic imaging unit 100 does not output a certain state signal according to an embodiment, the ultrasonic imaging unit 200 irradiates ultrasonic waves, collects echo ultrasonic waves, and continuously generates an ultrasonic image in step 733.

In accordance with a method for controlling the combined imaging apparatus as shown in FIG. 13, the ultrasonic imaging unit 200 may be controlled using both state signals of the photoacoustic imaging unit 100 and the ultrasonic imaging unit 200.

While the photoacoustic imaging unit 100 and the ultrasonic imaging unit 200 are operated according to a predetermined control sequence, the photoacoustic imaging unit 100 starts operation such that the state signal of the photoacoustic imaging unit 100 is output in step 740.

If the output state signal is the active or pre-active state signal in step 741, the ultrasonic imaging unit 200 or the controller 300 may first determine the operation state of the ultrasonic imaging unit 200.

If the ultrasonic imaging unit 200 is in the ultrasound irradiation state in which ultrasonic waves are irradiated to the target part (t) as shown in FIG. 9A in step 751, the ultrasonic imaging unit 100 stops operation in step 752. In this case, the control command (c3) for interrupting the operation of the ultrasonic imaging unit 200 may be generated and transmitted to the ultrasonic imaging unit 100.

If the ultrasonic imaging unit 200 is in the ultrasound collection state or the next state (for example, the image processing state) as shown in FIG. 9B in step 761, the ultrasonic imaging unit 200 does not stop ultrasound collection or image processing in step 762. If the ultrasonic imaging unit 200 completes the ultrasonic collection or the next state in step 763, the ultrasonic imaging unit 200 may not perform the ultrasound irradiation operation any more in step 764. Likewise, the controller 300 may generate a control command for controlling the ultrasonic imaging unit 100, and may transmit the control command to the ultrasonic imaging unit 100.

Meanwhile, if the state signal of step 740 is a stop signal, i.e., if the photoacoustic imaging unit 100 is in the stop state in step 771, the operation of the ultrasonic imaging unit 200 does not overlap the operation of the photoacoustic imaging unit 100, such that ultrasound irradiation and collection of echo ultrasonic waves can be maintained in step 772.

As is apparent from the above description, the combined imaging apparatus and the method for controlling the same according to the embodiments may prevent overlap or collision between operations of heterogeneous imaging apparatuses due to a variance in operation time of the heterogeneous imaging apparatuses.

The combined imaging apparatus and the method for controlling the same according to the embodiments can minimize delay of an unnecessary standby time not expected when an image is captured by the heterogeneous imaging apparatuses.

Therefore, the combined imaging apparatus and the method for controlling the same according to the embodiments can basically prevent the occurrence of image distortion generated by the overlap or collision between operations of the heterogeneous imaging apparatuses, resulting in improved image accuracy.

The combined imaging apparatus and the method for controlling the same according to the embodiments can minimize complexity and design difficulty of a conventional time schedule which is configured in consideration of all the cases generated when the heterogeneous imaging apparatuses contained in the combined imaging apparatus are properly controlled to prevent the occurrence of image distortion.

In addition, the combined imaging apparatus and the method for controlling the same according to the embodiments can perform time-based independent control of the combined imaging apparatus including heterogeneous imaging apparatuses.

As a result, assuming that the above-mentioned combined imaging apparatus is a medical imaging diagnostic apparatus, it can prevent the occurrence of misdiagnosis caused by inaccuracy of a measured image.

Although a few embodiments of one or more exemplary embodiments have been shown and described, it would be appreciated by those skilled in the art that changes may be made in these embodiments without departing from the principles and spirit of the invention, the scope of which is defined in the claims and their equivalents.

What is claimed is:

1. A combined imaging apparatus comprising:
   a photoacoustic imaging unit to irradiate an energy beam to a target part;
   an ultrasonic imaging unit to generate an ultrasonic wave, irradiate the ultrasonic wave to the target part, and collect either an echo ultrasonic wave reflected from the target part to which the ultrasonic wave is irradiated or an ultrasonic wave generated from the target part in response to energy beam irradiation of the photoacoustic imaging unit; and
   a controller configured to decide an operation state of the photoacoustic imaging unit, to determine an operation of the ultrasonic imaging unit based on the decided operation state of the photoacoustic imaging unit, and to transmit a command to the ultrasonic imaging unit.

2. The combined imaging apparatus according to claim 1, wherein the controller is further configured to control the photoacoustic imaging unit and the ultrasonic imaging unit on the basis of a state-signal based control sequence.

3. The combined imaging apparatus according to claim 2, wherein the controller is further configured to determine the operation of the ultrasonic imaging unit on the basis of the operation state of the photoacoustic imaging unit while the photoacoustic imaging unit and the ultrasonic imaging unit are operated according to the state-signal based control sequence.

4. The combined imaging apparatus according to claim 1, wherein the photoacoustic imaging unit operates in at least one of an active state for energy beam irradiation and a pre-active state indicating a ready state for energy beam irradiation.

5. The combined imaging apparatus according to claim 4, wherein the controller is further configured to control the ultrasonic imaging unit to stop an ultrasound irradiation operation if the photoacoustic imaging unit is in the active state or in the pre-active state.

6. The combined imaging apparatus according to claim 4, wherein the controller is further configured to determine the operation of the ultrasonic imaging unit in response to the operation state of the ultrasonic imaging unit if the photoacoustic imaging unit is in the active state or in the pre-active state.

7. The combined imaging apparatus according to claim 6, wherein the controller is further configured to control the ultrasonic imaging unit to stop the ultrasound irradiation operation and perform only an operation for collecting of ultrasonic waves if the photoacoustic imaging unit is in the active state, to maintain operation of the ultrasound irradiation and the ultrasound collection if the photoacoustic imaging unit is in the pre-active state, and to control the ultrasound irradiation to stop operation if the ultrasound collection stops operation.

8. The combined imaging apparatus according to claim 3, wherein the controller is further configured to control the photoacoustic imaging unit to output a state signal indicating the operation state of the photoacoustic imaging unit if the photoacoustic imaging unit is in the active state or in the pre-active state.

9. The combined imaging apparatus according to claim 8, wherein the ultrasonic imaging unit is operated if the photoacoustic imaging unit does not output the state signal indicating the active state or the pre-active state.

10. The combined imaging apparatus according to claim 1, wherein a number of additional operation times to be performed by the ultrasonic imaging unit are decided if the photoacoustic imaging unit is in an active state or in a pre-active state.

11. The combined imaging apparatus according to claim 10, wherein the controller is further configured to control the ultrasonic imaging unit to operate according to the decided number of operation times of the ultrasonic imaging unit.

12. The combined imaging apparatus according to claim 1, wherein the photoacoustic imaging unit includes a sensor unit to detect the operation state of the photoacoustic imaging unit.

13. The combined imaging apparatus according to claim 12, wherein the sensor unit is a photo sensor for detecting the energy beam irradiated to the target part by the photoacoustic imaging unit.

14. The combined imaging apparatus according to claim 1, wherein the photoacoustic imaging unit generates a state signal indicating the operation state of the photoacoustic imaging unit on the basis of an elapse time.

15. A method for controlling a combined imaging apparatus which includes a photoacoustic imaging unit and an ultrasonic imaging unit, the method comprising:
   operating the ultrasonic imaging unit which receives at least one of an echo ultrasonic wave reflected from a target part and an ultrasonic wave generated from the target part by an energy beam irradiated to the target part by the photoacoustic imaging unit;
   outputting, by the photoacoustic imaging unit, a state signal indicating an operation state of the photoacoustic imaging unit;
   deciding an operation of the ultrasonic imaging unit according to the state signal generated from the photoacoustic imaging unit; and
   controlling the ultrasonic imaging unit in accordance with the decided operation of the ultrasonic imaging unit to generate and irradiate an ultrasound wave to the target part or to stop operation of the ultrasonic imaging unit.

16. The method according to claim 15, wherein the photoacoustic imaging unit is in an active state for energy beam irradiation or in a pre-active state indicating a ready state for energy beam irradiation.

17. The method according to claim 16, wherein the deciding the operation of the ultrasonic imaging unit according to the state signal generated from the photoacoustic imaging unit includes:
   deciding to stop the ultrasound irradiation operation of the ultrasonic imaging unit when the photoacoustic imaging unit is in the active state or in the pre-active state.

18. The method according to claim 17, wherein the deciding the operation of the ultrasonic imaging unit according to the state signal generated from the photoacoustic imaging unit includes:
   if the photoacoustic imaging unit is in the active state or in the pre-active state, confirming an operation state of the ultrasonic imaging unit; and
   deciding an operation of the ultrasonic imaging unit according to the confirmed operation state of the ultrasonic imaging unit.

19. The method according to claim 18, wherein the deciding the operation of the ultrasonic imaging unit according to the confirmed operation state of the ultrasonic imaging unit includes:
   if the ultrasonic imaging unit collects echo ultrasonic waves, maintaining the operation of the ultrasonic imaging unit.

20. The method according to claim 19, wherein the deciding the operation of the ultrasonic imaging unit according to the confirmed operation state of the ultrasonic imaging unit includes:
   if collection of the echo ultrasonic waves caused by the ultrasonic imaging unit is completed, stopping the ultrasound irradiation operation of the ultrasonic imaging unit.

21. The method according to claim 15, further comprising:
   if the photoacoustic imaging unit does not output the state signal, deciding to perform ultrasound irradiation by the ultrasonic imaging unit.

22. The method according to claim 15, wherein the deciding the operation of the ultrasonic imaging unit according to the state signal generated from the photoacoustic imaging unit includes:
   if the photoacoustic imaging unit is in an active state or in a pre-active state, deciding a number of additional operation times to be performed by the ultrasonic imaging unit; and
   operating the ultrasonic imaging unit the decided number of operation times.

23. The method according to claim 15, wherein the outputting the state signal indicating the operation state of the photoacoustic imaging unit includes:
   detecting the operation state of the photoacoustic imaging unit by a sensor unit of the photoacoustic imaging unit; and
   outputting a state signal indicating the operation state of the photoacoustic imaging unit according to the detected result.

24. The method according to claim 23, wherein the sensor unit is a photo sensor for detecting the energy beam irradiated to the target part by the photoacoustic imaging unit.

25. The method according to claim 15, wherein the outputting the state signal indicating the operation state of the photoacoustic imaging unit includes:
   after the photoacoustic imaging unit completes energy beam irradiation, starting a time count action; and
   if the counted time is identical to or longer than a predetermined state signal output time, outputting the state signal of the photoacoustic imaging unit,
   wherein the state signal is a state signal indicating an active state or a state signal indicating a pre-active state.

26. The method according to claim 15, wherein the outputting the state signal indicating the operation state of the photoacoustic imaging unit includes:
   outputting the state signal indicating the photoacoustic imaging unit's operation state generated on the basis of an elapsed time.

* * * * *